US011464433B2

(12) United States Patent
Rebec et al.

(10) Patent No.: US 11,464,433 B2
(45) Date of Patent: Oct. 11, 2022

(54) SYSTEMS AND METHODS FOR BIOSENSOR CROSS-CALIBRATION

(71) Applicant: WaveForm Technologies, Inc., Salem, NH (US)

(72) Inventors: Mihailo V. Rebec, Portland, OR (US); Ralph Dutt-Ballerstadt, Portland, OR (US)

(*) Notice: Subject to any disclaimer, the term of this patent is extended or adjusted under 35 U.S.C. 154(b) by 0 days.

(21) Appl. No.: 16/869,470

(22) Filed: May 7, 2020

(65) Prior Publication Data
US 2020/0352479 A1 Nov. 12, 2020

Related U.S. Application Data

(60) Provisional application No. 62/845,498, filed on May 9, 2019.

(51) Int. Cl.
*A61B 5/1495* (2006.01)
*A61B 5/145* (2006.01)
*A61B 5/00* (2006.01)

(52) U.S. Cl.
CPC .......... *A61B 5/1495* (2013.01); *A61B 5/0022* (2013.01); *A61B 5/14503* (2013.01); *A61B 5/14532* (2013.01); *A61B 5/7207* (2013.01); *A61B 5/74* (2013.01); *A61B 2560/0238* (2013.01); *A61B 2562/085* (2013.01)

(58) Field of Classification Search
CPC . A61B 5/1495; A61B 5/0022; A61B 5/14503; A61B 5/14532; A61B 5/7207; A61B 5/74; A61B 2560/0238; A61B 2562/085
See application file for complete search history.

(56) References Cited

U.S. PATENT DOCUMENTS

2005/0239154 A1   10/2005  Feldman
2009/0192366 A1*  7/2009  Mensinger ......... A61B 5/14532
                                                         600/301
2012/0289804 A1   11/2012  Yao
(Continued)

OTHER PUBLICATIONS

Patent Cooperation Treaty: International Search Report and Written Opinion for PCT/US2020/031948 dated Sep. 4, 2020; 8 pages.

*Primary Examiner* — Sean P Dougherty
*Assistant Examiner* — Alexander H Connor
(74) *Attorney, Agent, or Firm* — Schwabe, Williamson & Wyatt, PC

(57) ABSTRACT

Embodiments provide for methods, systems, apparatus and computer readable media for calibrating an analyte sensor upon insertion into tissue of a subject based at least in part on parameters obtained from another analyte sensor already calibrated and previously inserted into the tissue of the subject. As an example, a method may include predicting a background current associated with the newly inserted sensor, subtracting the background current from a current measured by the newly inserted sensor, and converting the subtracted current to a glucose value, the converting based at least in part on the parameters obtained from the previously inserted analyte sensor. In this way, the newly inserted sensor may be calibrated without relying on actual blood-based analyte measurements, and accuracy and sensitivity of the newly inserted sensor may be improved.

16 Claims, 10 Drawing Sheets

(56) References Cited

U.S. PATENT DOCUMENTS

| | | | |
|---|---|---|---|
| 2015/0164383 A1 | 6/2015 | Varsavsky | |
| 2016/0000360 A1* | 1/2016 | Feldman | A61B 5/1495 600/309 |
| 2017/0128007 A1* | 5/2017 | Hayter | A61B 5/6849 |

* cited by examiner

SYSTEMS AND METHODS FOR BIOSENSOR CROSS-CALIBRATION

CROSS-REFERENCE TO RELATED APPLICATION

This application claims the priority benefit of the earlier filing date of U.S. Provisional Patent Application No. 62/845,498, filed May 9, 2019, which is hereby incorporated herein by reference in its entirety.

TECHNICAL FIELD

Embodiments herein relate to the field of biosensors, and, more specifically, to the calibration of an analyte sensor to obtain consistent readings and reduce background artifacts.

BACKGROUND

Continuous sensors, such as continuous glucose monitoring (CGM) sensors, are used to measure data continuously, e.g., in a continuous data stream and/or sampled data points over a time interval. Typically, the data is inconsistent for a period post insertion as the sensor acclimates to the in vivo conditions and background currents stabilize. Currently, all CGM systems require a so-called run-in time, and thus, immediately after insertion of the sensor the measurement is not reliable. Therefore, it would be advantageous if the sensor and associated electronics could compensate for signal artifacts post insertion.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1:
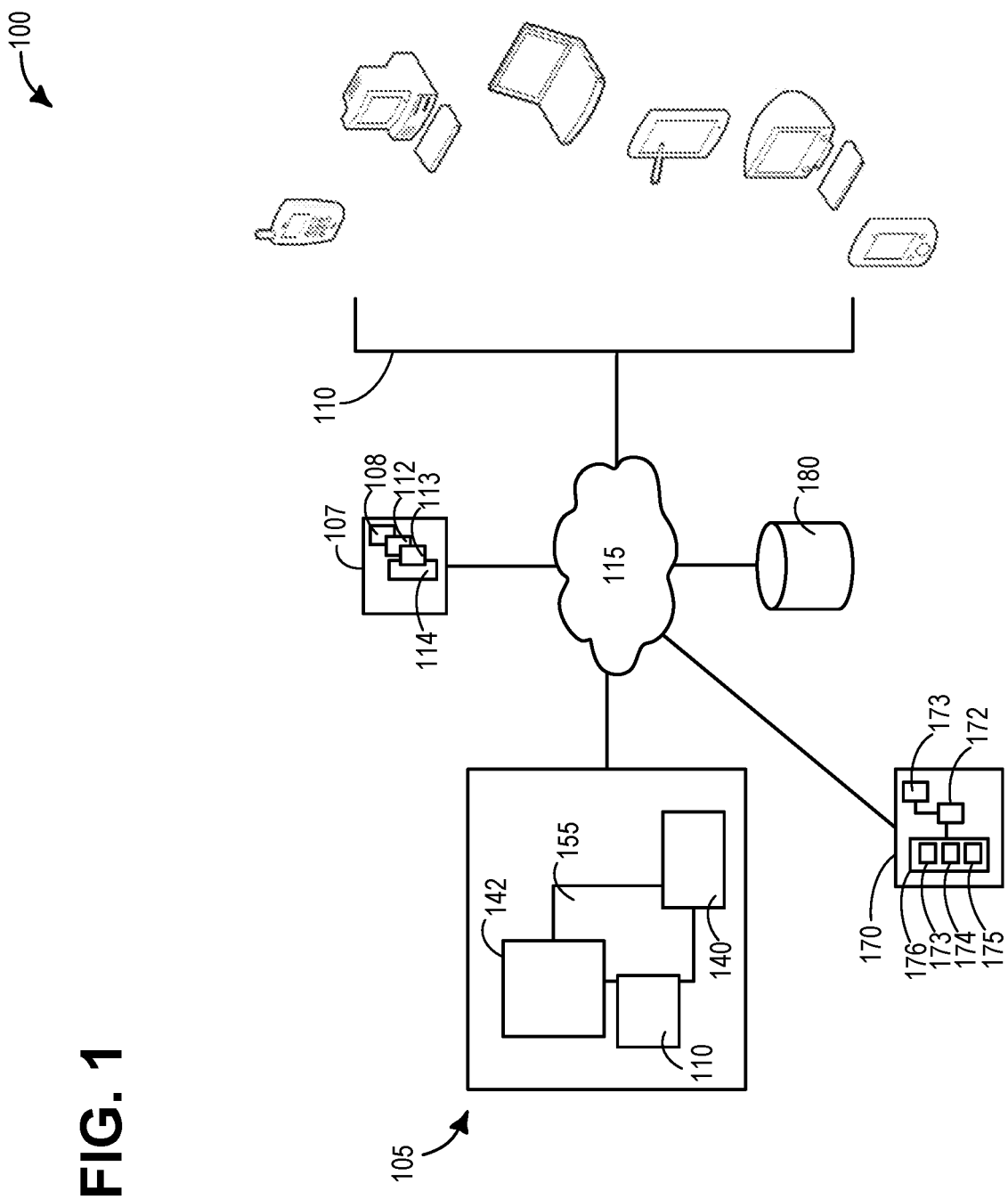
FIG. 1 is a schematic diagram of a networked CGM system for cross-calibration of an analyte sensor, in accordance with embodiments herein.

In the following detailed description, reference is made to the accompanying drawings which form a part hereof, and in which are shown by way of illustration embodiments that may be practiced. It is to be understood that other embodiments may be utilized, and structural or logical changes may be made without departing from the scope. Therefore, the following detailed description is not to be taken in a limiting sense.

Various operations may be described as multiple discrete operations in turn, in a manner that may clarify embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Continuous glucose monitoring (CGM) technology has been used in the management of diabetes for many years. Traditional devices (e.g., sensors) use enzymatic methods (e.g., glucose oxidase-based conversion of glucose to hydrogen peroxide that reacts with platinum to generate an electrical signal) to measure glucose concentration and provide sample information. In some applications, the CGM sensor may be a critical component of a closed loop insulin delivery system and, as such, must be selective, rapid, predictable and acceptable for continuous patient use.

Some of the issues facing the continuing development of continuous CGM systems include but are not limited to calibration requirements for the inserted glucose sensor and the erratic performance of the glucose sensor within the first 12 hours after insertion. Several factors may contribute to the erratic performance of the sensor within this 12-hour period. One example includes the equilibration of the skin/tissue to the damaging process of the insertion of the sensor. Another example includes the warmup of stabilization phenomena related to the sensor. Yet another example includes the presence of interstitial fluid components such as proteins that settle on the outside of the sensor over time. Still further examples include acute and/or chronic immune responses that occur in a subject responsive to sensor insertion. Such processes may have an impact on the type and quality of signal that is generated by the sensor.

Other issues with the accuracy of CGM sensors relate to signal artifacts and dynamic sensor behavior changes over time. Operational lifetimes of current CGM systems are approximately 14 days or less. However, increasing wear times to at least 20 days or longer, or even 30 days or longer, may be desirable.

The inventors herein have recognized the above-mentioned issues and have developed methods and systems to at least partially address them. Accordingly, embodiments herein provide a method for biosensor calibration. The method comprises initiating a crossover calibration procedure, and over a first time duration, measuring a first current from a first biosensor and measuring a second current from a second biosensor, the first biosensor having been inserted into tissue of a subject prior to insertion of the second biosensor. The method further comprises converting the first current to a first analyte value, comparing the first current to the second current, and obtaining a second analyte value based on the comparing. In this way, the second biosensor may be calibrated. It may be understood that the first analyte value may comprise one or more first analyte values, and the second analyte value may comprise one or more second analyte values.

For the method, the first biosensor may be inserted into the tissue of the subject at least one day but less than thirty days before insertion of the second biosensor. The first biosensor may be calibrated prior to initiating the crossover calibration, and the calibration of the first biosensor may be based on one or more actual blood analyte values obtained from blood of the subject. The first time duration may be at least one minute but not more than sixty minutes, and the converting of the first current to the first analyte value may occur between five seconds and sixty seconds from a starting point of the first-time duration.

For the method, comparing the first current to the second current and obtaining a calibrated current may further comprise predicting a first background current that is some fraction of the second current as a function of time over a second time duration, the second time duration extending beyond the first time duration. The method may further include subtracting the background current from the second current over the second time duration to obtain a subtracted second current, and based at least in part on one or more of the subtracted second current, the first current, and the first analyte value, creating a conversion operation for converting the subtracted second current to the second analyte value. Each of the first current and the second current may continue to be also measured over the second duration. In some examples, predicting the background current may be based at least in part on one or more of the second current, the first current and the first analyte value. In some examples, the second time duration extends to twelve hours post insertion of the second biosensor. In some examples, the method further comprises retrieving historical data pertaining to an analyte sensitivity for one or more other biosensors previously worn by the subject, and applying a correction factor derived from the analyte sensitivity when generating the second analyte value to increase sensitivity of the second biosensor.

For the method, comparing the first current to the second current and generating the second analyte value may further comprise predicting a second background current that is some fraction of the second current as a function of time over a third time duration. The third time duration may extend beyond the first time duration and the second time duration, and the second current may continue to be measured during the third time duration. The method may include subtracting the second background current from the second current measured over the third time duration to obtain the subtracted second current, and using the conversion procedure to generate the second analyte value for the second biosensor based on the subtracted second current determined during the third time duration as input. In such an example, the second background current may be based on data collected from any number of biosensors of a same type as the first and/or second biosensor and that is related to background current in the second biosensor over the third time duration. In some examples, the third time duration may extend out to greater than 15 days, or greater than 20 days (e.g., 21 days), or greater than 25 days, or greater than 30 days (e.g., 31 days) following insertion of the second biosensor. In this way, accurate second analyte values may be obtained throughout the lifetime of the second sensor.

For the method, each of the first biosensor and the second biosensor may comprise glucose biosensors, and in such an example, the first analyte value and the second analyte value may be understood to correspond to glucose values.

In another embodiment a system for delivery of insulin to a subject in need thereof, is provided. The system may comprise a first glucose biosensor, a second glucose biosensor, and a mobile computing device. The mobile computing device may include a processor, and the processor may storing instructions in non-transitory memory that, when executed, cause the processor to receive a notification that the second glucose biosensor has been inserted into the subject while the first glucose biosensor is already inserted into the subject, and initiate a cross calibration procedure within a determined amount of time subsequent to receiving the indication. The instructions may further cause the processor to obtain a first current from the first glucose sensor and a second current from the second biosensor, convert the first current to a first glucose value, and predict a background current associated with the second sensor based at least in part on one or more of the first current, the second current and the first glucose value. The instructions may further cause the processor to subtract the background current from the second current to obtain a subtracted second current, and convert the calibrated current to a second glucose value. The instructions may further cause the processor to provide a set of instructions pertaining to delivery of insulin to the subject based on the second glucose value. For such a system, it may be understood that the first glucose value may comprise one or more first glucose values, and the second glucose value may comprise one or more second glucose values.

In an example of the system, the system may further comprise an insulin delivery unit in communication with the mobile computing device, the insulin delivery unit including at least an insulin pump and an infusion set, the infusion set fluidically coupled to the insulin pump via a tubing. In such an example, the processor of the mobile computing device may store further instructions to send the set of instructions pertaining to delivery of insulin to the subject to the insulin delivery unit for delivering insulin to the subject via the infusion set by controlling operation of the insulin pump.

For such a system, in an additional or alternative example, the mobile computing device may further comprise a display. The processor of the mobile computing device may store further instructions to communicate the set of instructions pertaining to delivery of insulin to the subject via the display.

For such a system, the processor of the mobile computing device may store further instructions to compare the first glucose value to the second glucose value. Responsive to an indication that the second glucose value is correlated within a predetermined threshold of the first glucose value, the set of instructions pertaining to delivery of insulin to the subject based on the second glucose value may be provided. For such a system, the processor of the mobile computing device may store further instructions to provide an alert to the subject that the first glucose biosensor can be removed in response to the indication that the second glucose value is correlated within the predetermined threshold of the first glucose value.

For such a system, the processor of the mobile computing device may store further instructions to predict the background current between one minute and 60 minutes following initiation of the cross calibration procedure, and subtract the background current from the second current for scale the second current to the first current for up to two days following initiation of the cross calibration procedure. However, it may be understood that, as discussed with regard to other embodiments herein, in some examples, background current (e.g., a second background current) may continue to be subtracted from the second current for a period ranging between 15-30 days or even slightly longer (e.g., 31 days, 32 days, 33 days, 34 days, 35 days, etc.). In such an example where longer time periods are included, it may be understood that the background current (e.g., second background current) may be modeled based on relevant data obtained from one or more earlier worn sensor(s) of a similar type as each of the first and second glucose biosensors.

Embodiments herein also provide for an apparatus for calibrating a biosensor inserted into tissue of a subject. The apparatus may comprise a mobile computing device including a processor, the processor storing instructions in non-transitory memory. When executed, the instructions may cause the processor to, while a first sensor is inserted into the tissue of the subject, detect insertion of a second sensor into the tissue, and initiate a cross calibration procedure of the second sensor responsive to the detecting. The instructions may further cause the processor to obtain a first current from the first sensor and a second current from the second sensor and convert the first current into a first analyte value. In response to an indication that predetermined conditions are met for modeling a non-glucose driven background current associated with the second sensor, the instructions may cause the processor to predict the non-glucose driven background current for the second sensor over a predetermined time duration. During the predetermined time duration, the instructions may cause the processor to subtract the non-glucose driven background current from the second current to obtain a subtracted second current for the second sensor, and convert the subtracted second current to a second analyte value. For such an apparatus, it may be understood that the first analyte value may comprise one or more first analyte values, and the second analyte value may comprise one or more second analyte values.

For such an apparatus, the processor may store further instructions to predict the non-glucose driven background current based on the second current measured prior to the predetermined conditions being met, and at least in part based on one or more of the first current and the first analyte value obtained prior to the predetermined conditions being met. In some additional or alternative examples, the processor may store further instructions to predict the non-glucose driven background current based on a previously generated pattern of background current changes learned over time from a plurality of other analyte sensors inserted into the subject at earlier times.

For such an apparatus, in an example, the indication that predetermined conditions are met for modeling the non-glucose driven background current may occur between one minute and sixty minutes after initiation of the cross-calibration procedure. Further, the predetermined time duration in which the non-glucose driven background current is subtracted from the second current may be at least two hours and up to sixty-four hours. In some examples, the non-glucose driven background current may be modeled for greater than sixty-four hours, for example an entire wear time of the second sensor. Such longer term modeling of the background current may rely on learned background currents associated with previous sensors of the same type, worn previously by the same subject. The entire wear time for sensors of the present disclosure may be 21 days or greater. In one example, the entire wear time of sensors of the present disclosure may comprise thirty days, or a time duration between 30-35 days.

For such an apparatus, obtaining the subtracted second current and converting the subtracted second current to the second analyte value may further comprise the following. Specifically, via further instructions stored in non-transitory memory of the processor, the processor may recall one or more previously learned analyte sensitivity values from prior use by the subject of other analyte sensor(s), and may apply a correction procedure to obtain an accurate analyte sensitivity for the second sensor. For example, sensitivity changes as discussed herein may be understood to relate to a change in measured current as a function of a change in analyte concentration (e.g., nA/(mg/dL)). Thus, it may be understood that in addition to longer term modeling of background current as discussed above, sensitivity changes learned from one or more previously worn sensors by the same subject may similarly be modeled (e.g., out to 30 days of use). The longer term modeling of sensitivity changes may then be used, for example via the correction procedure that relies on one or more values obtained via the longer term modeling of the sensitivity changes, to obtain the accurate analyte sensitivity for the second sensor while the second sensor is being worn. In this way, the apparatus may provide for a calibration approach that does not rely on blood analyte measurements for calibration, even for sensors worn up to and even exceeding 30 days of use. Embodiments herein also provide for a non-transitory computer-readable storage medium with an executable program stored thereon for biosensor calibration. The executable program may instruct a microprocessor to perform one or more steps. One step may include detecting that a second analyte sensor has been inserted into skin of a subject following insertion of a first analyte sensor into the skin of the subject, where insertion of the first analyte sensor occurs between one and thirty days prior to the second analyte sensor being inserted. Another step may include initiating a cross calibration procedure based on the detecting. Another step may include retrieving a first current from the first analyte sensor and a second current from the second analyte sensor and converting the first current to a first analyte value within five seconds to sixty seconds of initiating the cross-calibration procedure. Another step may include determining that a current decay trend can be established for the second analyte sensor based on the second current within sixty seconds to one hour following initiation of the cross-calibration procedure. In response, another step may include predicting a background current (e.g., a first background current) extrapolated over a predetermined time duration based at least in part on the second current measured within sixty seconds to one hour following initiation of the cross-calibration procedure. Another step may include, over the predetermined time duration, subtracting the background current profile from the second current to obtain a subtracted second current. Another step may include converting the subtracted second current to a second analyte value, thereby calibrating the second analyte sensor. For such a non-transitory computer-readable storage medium, it may be understood that the first analyte value may comprise one or more first analyte values, and the second analyte value may comprise one or more second analyte values.

For such a non-transitory computer-readable storage medium the executable program may store further instructions to, during the predetermined time duration, continue to convert the first current to the first analyte value (provided the first analyte sensor remains embedded in the skin of the subject). The instructions may further include comparing the first analyte value during the predetermined time duration to the second analyte value. The instructions may further include determining that the second analyte sensor is effectively calibrated responsive to the first analyte value obtained during the predetermined time duration correlating within a predetermined threshold of the second analyte value.

For such a non-transitory computer-readable storage medium, the executable program may store further instructions to determine an appropriate amount of insulin to be injected into the subject based on the second analyte value, wherein each of the first analyte sensor and the second analyte sensor are glucose biosensors.

For such a non-transitory computer-readable storage medium the predetermined time duration may comprise between one hour and twelve hours. However, in other examples, the predetermined time duration may comprise between one hour and 30 days (or even out to 35 days). For example, in situations where the predetermined time duration extends past at least 6 hours, or at least 12 hours, or at least 20 hours, or at least 24 hours, then a second background current may be determined, for continued subtraction of the second measured current from the second background current similar to that discussed above. The second background current may be determined based on historical data retrieved from one or more other sensors of a same type, previously worn by the subject. In this way, sensor lifetime may be extended, for example out to 30 days or even greater in some examples.

Still further, for such a non-transitory computer-readable storage medium, the executable program may store further instructions to generate an analyte sensitivity based at least in part on the second analyte values for the second analyte sensor during the predetermined time period; retrieve one or more analyte sensor performance parameters from previous analyte sensor wear periods by the subject, the one or more analyte sensor performance parameters including a background current dataset and an analyte sensitivity determination dataset corresponding to a plurality of previously worn analyte sensors; and implement one or more correction procedures that rely on one or more of the background current dataset and the analyte sensitivity determination dataset to increase an accuracy of the analyte sensitivity for the second analyte sensor. Such a procedure may improve performance and may additionally or alternatively serve to reduce or eliminate any blood calibration steps associated with use of the second analyte sensor. It may be understood that the analyte sensitivity determination dataset may comprise analyte sensitivity determinations from any number of sensors of the same type previously worn by the subject. The analyte sensitivity determinations may be averaged or otherwise processed, for example via machine learning or deep learning methodologies, to learn analyte sensitivity changes over time, which may then be used to improve sensitivity for the sensor currently being worn by the subject.

With regard to the embodiments discussed above, it has herein been recognized that there are trends in an analyte sensor's signal that occurs over an initial 12 hour period and beyond after sensor insertion and/or activation. The trends include but may not be limited to background current changes and sensor sensitivity changes that both happen over time.

Background current as discussed herein refers to the current that is observed in a multi-electrode system (e.g., two or three electrode systems), such as a current commonly relied upon in a glucose sensor that is not directly related to the measurement of glucose levels. This signal may start quite high in the minutes just after the sensor is inserted into the skin and may then gradually go through an exponential drop over the next 6 to 12 hours (refer to Example 2 below). After that initial drop, the non-glucose related background signal may still vary over time but to a smaller degree than in the first 12 hours. As an example, a pattern for a background current signal for a glucose sensor post insertion may be a steep drop for about the first 6 hours followed by a shallower drop over the next 6 hours. The current signal may then continue to drop at a much more gradual pace and in a more linear manner for the next 5-6 days. A third pattern may then immerge, which is a gradual rise in the background current signal from about day 5 to about day 30. There are other patterns that may occur as well but are not easily modeled based on the initial decay or drop.

Producing a model of the behavior of this background or non-glucose related current (NGC) requires a high destiny of high-quality data. This can be a difficult measurement to make in an in vivo setting since there may not be an independent check as to what was causing the drop in the current, for example whether the current drop is based on a drop in glucose or if it comprises a true change in the NGC signal. Typically, such a check would require a determination of the blood glucose level using a blood glucose test meter. Discussed herein, a blood glucose test meter refers to a system whereby a subject pricks their finger to obtain a blood droplet, and then applies the blood droplet to a hand-held device that indicates actual blood glucose level.

To account for the difficulties in obtaining reliable data within this first 12-hour window, the inventors have herein developed a crossover calibration method, also referred to as a cross-calibration method, to differentiate between glucose level modulated current and non-glucose related current (NGC). In addition, the disclosed methodology allows for the calibration of the sensitivity of a newly inserted sensor with a glucose value or values as determined by a sensor that has already been working in the body for some period of time, for example a glucose sensor that may have already been calibrated, either by the methodology disclosed herein or another method, such as calibration by comparison to an actual blood glucose determination (e.g., test meter blood glucose determination). This calibration methodology used to convert the current value(s) from the new sensor to one or more glucose value(s) may be performed without the need for a separate blood glucose analysis. Thus, the methodology discussed herein enables serial calibration of analyte sensors, and in certain embodiments can be continued for the life of the subject or some shorter time period.

The ability to correct or model the background current changes and the sensor sensitivity changes that occur over time, either individually or cumulatively, may have a significant effect on the performance of the system. To date however, previous approaches have been of limited value. It is well documented that the performance of the continuous glucose monitor (CGM) sensors on day one is generally 30% to 50% worse than on any other day, for example, in terms of Median Absolute Relative Deviation (MARD) or Mean Absolute Deviation (MAD) analysis. For example, during a recent study elaborated in greater detail below, the inventors evaluated the MARD that was observed during in-clinic day one vs. the performance on the second in-clinic day which is generally day 4 of the clinical study. The MARD numbers for day 1 were 17.7% while the numbers on day 4 were 10.5%.

Briefly, the study was conducted using 15 subjects in a seven-day sensor wear study. Each subject was asked to wear two sensors and to carry receiving devices with them. The CGM sensors were inserted in the morning of day 1. Each subject then spent the next 12 hours having blood draws at 15-minute intervals. The glucose concentration of the plasma from the drawn blood was determined using a glucose analyzer (Yellow Springs Instrument). The first plasma glucose concentration between 90-180 mg/dl was used to calibrate to the CGM sensors. Those values were used to convert CGM current values into blood glucose equivalent glucose values.

The subjects continued to wear the CGM devices for the next three days. On day 4, over a 12-hour period blood draws at 15-minute intervals were repeated in a similar way as day 1. The subjects continued to wear the CGM devices for another the next three days. On Day 7 another 12 hours of blood sampling and testing was completed. At the end of the 12 hours the sensors were removed, and the study was terminated. The accuracy analysis of the study was based on comparing the CGM generated glucose concentrations with the ones generated on the YSI using the venous draw blood samples. Each day was treated as a separate set of data and MARD and MAD values were generated for each day. Based on these evaluations, the average MARD was determined for day 1 and for day 4. Given the rapid changes that occur in day 1 after the sensor is inserted, the MARD for day 1 is generally much higher than it is on day 4 or day 7.

Turning to FIG. 1, disclosed herein is an example networked continuous analyte monitoring (CAM) system 100, in accordance with embodiments herein. In examples where the CAM system 100 is used to monitor glucose levels in a subject over time, the CAM system may be referred to as continuous glucose monitoring (CGM) system 100. The networked CAM system 100 includes an analyte sensor computing device 105 in wired or wireless communication with one or more analyte sensing devices 107 via network 115. Discussed herein, the one or more analyte sensing device(s) 107 may also be referred to as analyte sensor(s), or simply, sensors. In examples where the analyte sensor(s) comprise glucose sensors, the analyte sensor(s) may be referred to as CGM sensor(s), glucose sensors, or simply, sensors. The networked CAM system 100 may also include other networked devices 110 (e.g., laptop, desktop computer, tablet, smartphone, servers, mass storage devices, etc.), which may be in wired or wireless communication with analyte sensor computing device 105 and/or the one or more analyte sensor(s) 107 via network 115. In some embodiments, the analyte sensor computing device 105 includes application software with executable instructions configured to transmit and receive information from network 115. The information can be transmitted to and/or received from another device, such as one or more networked devices 110 through network 115. In certain examples, the analyte sensor computing device 105 may also be capable of transmitting information about analyte measurements retrieved from one or more of analyte sensor(s) 107 of a subject to one or more of a doctors, other medical practitioner.

As depicted at FIG. 1, the CAM system 100 distributes and receives information to and from one or more networked devices (e.g., analyte sensor computing device 105, networked devices 110) through one or more of network 115. According to various embodiments, network 115 may be any network that allows computers to exchange data, for example for cloud-based storage of data generated (historical and current) and/or implementation of some, none or even all the methods disclosed herein. Depicted at FIG. 1 is database 180, which in some examples may comprise cloud-based data storage. In some embodiments, network 115 includes one or more network elements (not shown) capable of physically or logically connecting computers. The network 115 may include any appropriate network, including an intranet, the Internet, a cellular network, a local area network (LAN), a wide area network (WAN), a personal network or any other such network or combination thereof. Components used for such a system can depend at least in part upon the type of network and/or environment selected. Protocols and components for communicating via such a network are well known and will not be discussed herein in detail. In embodiments, communication over the network 115 are enabled by wired or wireless connections, and combinations thereof. Network 115 includes a wired or wireless telecommunication means by which network systems may communicate and exchange data. For example, network 115 is implemented as, or may be a part of, a storage area network (SAN), personal area network (PAN), a metropolitan area network (MAN), a local area network (LAN), a wide area network (WAN), a wireless local area network (WLAN), a virtual private network (VPN), an intranet, an Internet, a mobile telephone network, such as Global System for Mobile Communications (GSM), General Packet Radio Service (GPRS), cdmaOne, CDMA2000, Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), Long-Term Evolution (LTE), $3^{rd}$ generation mobile network (3G), 4th generation mobile network (4G), and/or 5th generation mobile network (5G) networks, a card network, Bluetooth, near field communication network (NFC), any form of standardized radio frequency, or any combination thereof, or any other appropriate architecture or system that facilitates the communication of signals, data, and/or messages (generally referred to as data). Throughout this specification, it should be understood that the terms "data" and "information" are used interchangeably herein to refer to text, images, audio, video, or any other form of information that can exist in a computer-based environment.

In an example embodiment, each of analyte sensor computing device 105 and networked devices 110 may comprise a device having a communication component capable of transmitting and/or receiving data over network 115. For example, each networked device 110 may comprise a server, personal computer, mobile device (for example, notebook computer, tablet computer, netbook computer, personal digital assistant (PDA), video game device, GPS locator device, cellular telephone, smartphone, or other mobile device), a television with one or more processors embedded therein and/or coupled thereto, or other appropriate technology that includes or is coupled to a web browser or other application for communicating via the network 115.

Analyte sensor computing device 105 may be any computing device, such as a smart phone, tablet, desktop computer, laptop, etc., for crossover-calibrating a sensor (e.g., analyte sensor(s) 107 at FIG. 1) inserted into the tissue of a subject, in accordance with embodiments herein. In embodiments, analyte sensor computing device 105 includes several components, such as one or more processors 140 and at least one sensor communication module 142, for example that is capable of communication with a sensor (e.g., analyte sensor(s) 107 at FIG. 1). In various embodiments, the one or more processors 140 each include one or more processor cores. In various embodiments, the at least one sensor communication module 142 is physically and electrically coupled to the one or more processors 140. In various embodiments, the at least one sensor communication module 142 is physically and/or electrically coupled to the one or more sensors, such as a first and/or second analyte sensor. In some examples, it may be understood that the analyte sensor computing device 105 and the analyte sensor 107 may comprise a single device, without departing from the scope of this disclosure. In further implementations, the sensor communication module 142 is part of the one or more processors 140. In various embodiments, analyte sensor computing device 105 includes printed circuit board (PCB) 155. For these embodiments, the one or more processors 140 and sensor communication module 142 is disposed thereon. Depending on its applications, the analyte sensor computing device 105 includes other components that may or may not be physically and electrically coupled to the PCB. These other components include, but are not limited to, a memory controller (not shown), volatile memory (e.g., dynamic random access memory (DRAM) (not shown)), non-volatile memory (not shown) such as read only memory (ROM), flash memory (not shown), an I/O port (not shown), (not shown), a digital signal processor (not shown), a crypto processor (not shown), a graphics processor (not shown), one or more antenna (not shown), a touch-screen display 110, a touch-screen display controller (not shown), a battery (not shown), an audio codec (not shown), a video codec (not shown), a global positioning system (GPS) device (not shown), a compass (not shown), an accelerometer (not shown), a temperature monitor, a gyroscope (not shown) (not shown), a speaker (not shown), a camera (not shown), and a mass storage device (such as hard disk drive, a solid state drive, compact disk (CD) (not shown), digital versatile disk (DVD) (not shown), a microphone (not shown), and so forth.

In some embodiments, the one or more processors 140 is operatively coupled to system memory through one or more links (e.g., interconnects, buses, etc.). In embodiments, system memory is capable of storing information that the one or more processors 140 utilizes to operate and execute programs and operating systems, including computer readable instructions for the method disclosed herein. In different embodiments, system memory is any usable type of readable and writeable memory such as a form of dynamic random access memory (DRAM). In embodiments, analyte sensor computing device 105 includes or is otherwise associated with various input and output/feedback devices to enable user interaction with the analyte sensor computing device 105 and/or peripheral components or devices associated with the analyte sensor computing device 105 by way of one or more user interfaces or peripheral component interfaces. In embodiments, the user interfaces include, but are not limited to a physical keyboard or keypad, a touchpad, a display device (touchscreen or non-touchscreen), speakers, microphones, sensors, such as glucose sensors, haptic feedback devices and/or one or more actuators, and the like.

In some embodiments, the analyte sensor computing device 105 can comprise a memory element (not shown), which can exist within a removable smart chip or a secure digital ("SD") card or which can be embedded within a fixed chip. In certain example embodiments, Subscriber Identity Component ("SIM") cards may be used. In various embodiments, the memory element may allow a software application resident on the device.

In embodiments, a I/O link connecting a peripheral device to the analyte sensor computing device 105 is protocol-specific with a protocol-specific connector port that allows a compatible peripheral device to be attached to the protocol-specific connector port (i.e., a USB keyboard device would be plugged into a USB port, a router device would be plugged into a LAN/Ethernet port, etc.) with a protocol-specific cable. Any single connector port would be limited to peripheral devices with a compatible plug and compatible protocol. Once a compatible peripheral device is plugged into the connector port, a communication link would be established between the peripheral device and a protocol-specific controller.

In embodiments, a non-protocol-specific connector port is configured to couple the I/O interconnect with a connector port of the analyte sensor computing device 105, allowing multiple device types to attach to the analyte sensor computing device 105 through a single physical connector port. Moreover, the I/O link between the analyte sensor computing device 105 and the I/O complex is configured to carry multiple I/O protocols (e.g., PCI Express®, USB, DisplayPort, HDMI, etc.) simultaneously. In various embodiments, the connector port is capable of providing the full bandwidth of the link in both directions with no sharing of bandwidth between ports or between upstream and downstream directions. In various embodiments, the connection between the I/O interconnect and the analyte sensor computing device 105 supports electrical connections, optical connections, or both.

In some embodiments, the one or more processors 140, flash memory, and/or a storage device includes associated firmware storing programming instructions configured to enable the analyte sensor computing device 105, in response to execution of the programming instructions by one or more processors 140, to practice all or selected aspects of a method of crossover calibrating a sensor (e.g., analyte sensor(s) 107 at FIG. 1) inserted into the tissue of a subject using a computing device, in accordance with embodiments of the present disclosure.

In embodiments, the sensor communication module 142 may enable wired and/or wireless communications for the transfer of data to and from the analyte sensor computing device 105, for example to and/or from one or more sensors, (e.g., analyte sensor(s) 107 at FIG. 1). As one example, sensor communication module 142 may comprise a transmitter and/or a transmitter/receiver. In some examples, the transmitter and/or transmitter/receiver may be coupled, for example physically and/or electrically, to one or more sensors (e.g., glucose sensor(s)).

In various embodiments, the analyte sensor computing device 105 also includes a network interface configured to connect the analyte sensor computing device 105 to one or more networked computing devices wirelessly via a transmitter and a receiver (or optionally a transceiver) and/or via a wired connection using a communications port. In embodiments, the network interface and the transmitter/receiver and/or communications port are collectively referred to as a "communication module". In embodiments, the wireless transmitter/receiver and/or transceiver may be configured to operate in accordance with one or more wireless communications standards. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In embodiments, the analyte sensor computing device 105 includes a wireless communication module for transmitting to and receiving data, for example for transmitting and receiving data from a network, such as a telecommunications network. In examples, the communication module transmits data, including video data, though a cellular network or mobile network, such as a Global System for Mobile Communications (GSM), General Packet Radio Service (GPRS), cdmaOne, CDMA2000, Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), Long-Term Evolution (LTE), 3rd generation mobile network (3G), 4th generation mobile network (4G), and/or 5th generation mobile network (5G) networks. In embodiments, the system 100 is directly connect with one or more devices via the direct wireless connection by using, for example, Bluetooth and/or BLE protocols, WiFi protocols, Infrared Data Association (IrDA) protocols, ANT and/or ANT+ protocols, LTE ProSe standards, and the like. In embodiments, the communications port is configured to operate in accordance with one or more known wired communications protocol, such as a serial communications protocol (e.g., the Universal Serial Bus (USB), FireWire, Serial Digital Interface (SDI), and/or other like serial communications protocols), a parallel communications protocol (e.g., IEEE 1284, Computer Automated Measurement And Control (CAMAC), and/or other like parallel communications protocols), and/or a network communications protocol (e.g., Ethernet, token ring, Fiber Distributed Data Interface (FDDI), and/or other like network communications protocols).

In embodiments, the analyte sensor computing device 105 is configured to run, execute, or otherwise operate one or more applications. In embodiments, the applications include native applications, web applications, and hybrid applications. For example, the native applications are used for operating the analyte sensor computing device 105, sensor(s) (e.g., sensors 107 at FIG. 1) coupled to the analyte sensor computing device 105, and other like functions of the analyte sensor computing device 105. In embodiments, native applications are platform or operating system (OS) specific or non-specific. In embodiments, native applications are developed for a specific platform using platform-specific development tools, programming languages, and the like. Such platform-specific development tools and/or programming languages are provided by a platform vendor. In embodiments, native applications are pre-installed on analyte sensor computing device 105 during manufacturing, or provided to the analyte sensor computing device 105 by an application server via a network (e.g., network 115 at FIG. 1). Web applications are applications that load into a web browser of the analyte sensor computing device 105 in response to requesting the web application from a service provider. In embodiments, the web applications are websites that are designed or customized to run on a computing device by taking into account various computing device parameters, such as resource availability, display size, touch-screen input, and the like. In this way, web applications may provide an experience that is similar to a native application within a web browser. Web applications may be any server-side application that is developed with any server-side development tools and/or programming languages, such as PHP, Node.js, ASP.NET, and/or any other like technology that renders HTML. Hybrid applications may be a hybrid between native applications and web applications. Hybrid applications may be a standalone, skeletons, or other like application containers that may load a website within the application container. Hybrid applications may be written using website development tools and/or programming languages, such as HTML5, CSS, JavaScript, and the like. In embodiments, hybrid applications use browser engine of the analyte sensor computing device 105, without using a web browser of the analyte sensor computing device 105, to render a website's services locally. In some embodiments, hybrid applications also access computing device capabilities that are not accessible in web applications, such as the accelerometer, camera, local storage, and the like.

Any combination of one or more computer usable or computer readable medium(s) may be utilized with the embodiments disclosed herein. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium can even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computing device, partly on the user's computing device, as a stand-alone software package, partly on the user's computing device and partly on a remote computer or entirely on the remote computer or server. In the latter scenario, the remote computer may be connected to the user's computing device, through any type of network, including a local area network (LAN) or a wide area network (WAN), or the connection may be made to an external computing device, (for example, through the Internet using an Internet Service Provider), or wireless network, such as described above.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

In various embodiments, an article of manufacture may be employed to implement one or more methods as disclosed herein. The article of manufacture may include a computer-readable non-transitory storage medium and a storage medium. The storage medium may include programming instructions configured to cause an apparatus to practice some or all aspects a method of conducting cross-calibration using a computing device, in accordance with embodiments of the present disclosure.

The storage medium may represent a broad range of persistent storage medium known in the art, including but not limited to flash memory, optical disks or magnetic disks. The programming instructions, in particular, may enable an apparatus, in response to their execution by the apparatus, to perform various operations described herein. For example, the storage medium may include programming instructions configured to cause an apparatus to practice some or all aspects of a method of conducting calibrating an analyte sensor (e.g., sensor(s) 107 at FIG. 1) using a computing device (e.g., analyte sensor computing device 105 at FIG. 1), in accordance with embodiments of the present disclosure.

Analyte sensing device 107 may comprise an analyte sensing element 114. In some examples, analyte sensing element 114 may comprise one or more wire(s) or electrode(s) for translating an analyte (e.g., glucose) concentration into a representative electrical signal. Analyte sensing device 107 may further comprise a communication module 108 (e.g., transmitter, receiver, or transceiver) for communicating data (wired or wirelessly) and other information over network 115. In some examples, analyte sensing device 107 may further include a microprocessor 112 and a printed circuit board 113, similar to that discussed above for the analyte sensor computing device. Other components of analyte sensing device 107 that are not shown may include one or more of a memory controller, volatile memory (e.g., DRAM), non-volatile memory (e.g., ROM), flash memory, etc.

In some embodiments where CAM system 100 is configured as a CGM system, the system may in some examples include an insulin delivery unit 170. Insulin delivery unit 170 may be comprised of at least three parts, including but not limited to insulin pump 171, tubing 172 and infusion set 173. In an embodiment, insulin pump 171 may be battery powered and may contain (or be fluidically coupled to) an insulin reservoir (e.g., container), a pumping mechanism (e.g., pump driven by a small motor) and one or more buttons and/or touch screen (not shown) to program insulin delivery. In some examples, insulin pump 171 may receive instructions for insulin delivery over network 115, from one of analyte sensor computing device 105 or analyte sensing device 107. The instructions may be based on glucose concentrations as obtained via analyte sensing device 107. In such an example, it may be understood that insulin delivery unit 170 may operate in a closed-loop fashion with other components of CGM system 100 (e.g., analyte sensor computing device 105 and analyte sensing device 107) to mimic the way a pancreas works. It may be understood that each of insulin pump 171, tubing 172 and infusion set 173 may be coupled to each other in order to enable insulin pump 171 to deliver insulin to a subject by way of tubing 172 and infusion set 173. While insulin pump 171 may be battery powered, it may be understood that in some additional or alternative examples insulin pump 171 may be powered by electrically coupling insulin pump 171 to an external power source.

In some examples, insulin pump 171 may include buttons and/or a touch screen (not shown) for programming insulin delivery parameters. In another additional or alternative example, as mentioned above, insulin pump 171 may receive instructions for insulin delivery over network 1 15. Accordingly, in some examples insulin pump 171 may include a communication module 176 (e.g., receiver, or transceiver) capable of receiving and/or sending information (wired or wirelessly) over network 115, printed circuit board 174, and microprocessor 175. Other components of insulin pump 171 that are not shown may include one or more of a memory controller, volatile memory (e.g., DRAM), non-volatile memory (e.g., ROM), flash memory, etc.

Tubing 172 may in some examples comprise a thin tube fluidically coupled to each of the insulin reservoir and infusion set 173. Tubing 172 may be plastic, teflon, etc. Infusion set 173 may comprise componentry made of teflon and/or steel, and may attach to skin of a subject by way of an adhesive patch. The infusion set 173 may include a short thin tubing (e.g., cannula) that is inserted to skin via a needle housed within the cannula. After insertion, the needle may be removed and the thin cannula may remain under the skin. It may be understood that the above description relates to an example infusion set, but other similar infusion sets may be used interchangeably without departing from the scope of this disclosure.

Figure 2:
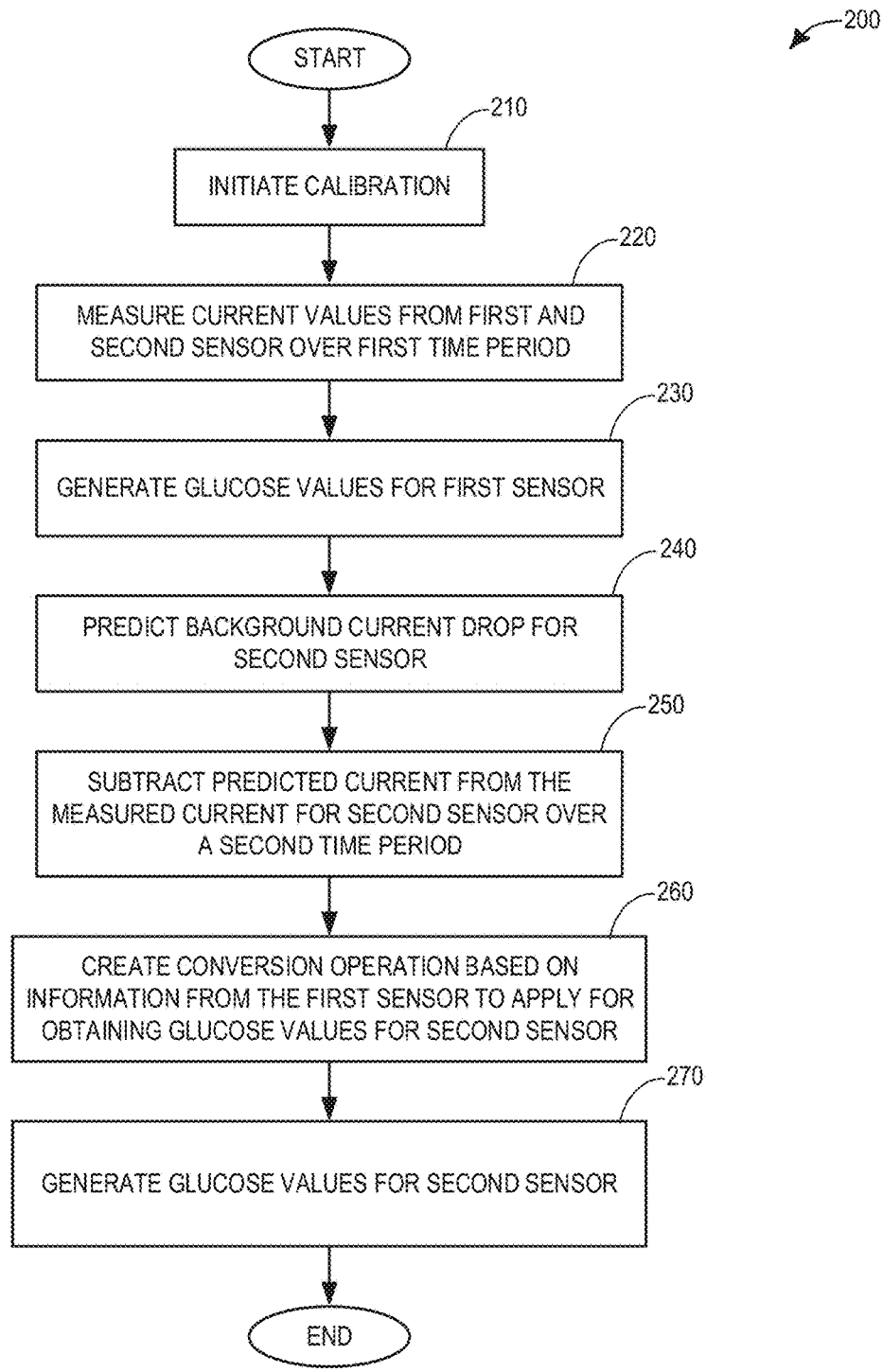
FIG. 2 is flow chart showing an example method for cross-calibration of a sensor using a computing device, in accordance with disclosed embodiments.

Turning now to FIG. 2, an example method 200 is shown for cross-calibrating an analyte sensor, such as a CGM sensor (e.g., sensor(s) 107 at FIG. 1). Method 200 may be an in vivo method of cross-calibrating the sensor. Specifically, method 200 may comprise a computer implemented method for cross-calibrating a second sensor inserted into the tissue of a subject, based on information/data retrieved from at least a first sensor already inserted into the tissue of the subject and which has previously been calibrated. Method 200 may comprise software instructions stored on a non-transitory computer readable medium that, when executed by a processor, cause the processor to perform the instructions to cross-calibrate the second sensor.

Method 200 begins at 210, and includes initiation of the crossover calibration event. This may be initiated in a myriad of ways. For example, a user may activate the event with their CGM device, also referred to herein as an analyte sensor, for example upon insertion of a new sensor. Calibration initiation may in one example be user initiated (e.g., via an actuator associated with the CGM device) or, in another example, recognized automatically by the CGM device (e.g., an actuator that is actuated upon insertion). Additionally or alternatively, calibration may be initiated via an application that the user has on a computing device (e.g., analyte sensor computing device 105 at FIG. 1), such as a smartphone. In some examples, the computing device may prompt the user to insert a new sensor, and calibration of the sensor may be initiated thereafter (automatically upon insertion, based on user confirmation, etc.). For example, such a prompt may be based on one sensor nearing the end of a normal wear cycle. The end of a normal wear cycle may comprise 14 days, however in other examples the end of the normal wear cycle may be greater than or less than 14 days (e.g., 30 days), without departing from the scope of this disclosure.

In another example, such a prompt may be initiated based on some issue with the performance of the sensor being presently used by the user. For example, responsive to an indication of degradation of the sensor, calibration of the sensor may be initiated. In another example, the calibration initiation event may even be initiated at a predetermined time after insertion (e.g., 30 seconds, 1 minute, 5 minutes, 10 minutes, 20 minutes, 30 minutes, 45 minutes, one hour, two hours, etc.), as opposed to immediately upon insertion. As one example, a sensor insertion event may be relayed to the analyte sensor computing device (e.g., analyte sensor computing device 105 at FIG. 1), and a timer associated with the analyte sensor computing device may be initiated. After a predetermined time period elapses, the analyte sensor computing device may command the initiation of the calibration routine.

In some examples, the time at which calibration is initiated following sensor insertion may be based on one or more user-specific parameters that have been learned or otherwise inferred over time. For example, although this disclosure is written with respect to glucose sensors, it is contemplated that the disclosed methods could be applied to other sensors, such as sensors that track chronic disease conditions, for examples sensors that detect creatinine, uric acid, potassium, sodium, urea, and/or a variety of drugs and their metabolites. Other examples include acetyl choline, amylase, bilirubin, cholesterol, chorionic gonadotropin, creatine kinase, DNA, fructosamine, glucose, glutamine, growth hormones, hormones, keytones, lactate, peroxide, prostate-specific antigen, prothrombin, RNA, thyroid stimulating hormone, troponin, etc. In some examples, concentration of drugs including but not limited to antibiotics (e.g., gentamicin, vancomycin, etc.), digitoxin, digoxin, drugs of abuse, theophylline, warfarin, etc., may be determined.

In certain embodiments a pattern of glucose levels may established over time for a user or subject, such that the system (e.g., CGM system 100 at FIG. 1) utilized learns how a subject's glucose levels change. In embodiments, these patterns are stored and may be called up once an individual has been identified with their login info and/or initiation event. These patterns may then be used to augment the background correction methodology discussed herein and the function of the overall algorithm of FIG. 2. This data may be stored in the smart device (e.g., analyte sensor computing device 105 at FIG. 1), or in the cloud or other storage database (e.g., database 180 at FIG. 1), as examples.

Responsive to calibration initiation, method 200 proceeds to 220. At 220, method 200 includes measuring and recording an electrical current (e.g., one or more current values) from a first analyte sensor, over a first determined time period (e.g., 1 minute, 5 minutes, 20 minutes, 30 minutes, 45 minutes, 60 minutes, 2 hours, etc.). It may be understood that the first sensor comprises a sensor that has been inserted into the subject for a sufficient period of time (e.g., one day, two days, three days, four days, five days, six days, seven days, greater than one day but less than 14 days, greater than 7 days but less than 14 days, greater than 14 days but less than 30 days, etc.) such that electrical current value(s) from the first sensor are stable and are not otherwise drifting with respect to the actual or real glucose value(s) occurring in the subject. It may be understood that electrical current value(s) that are stable with respect to the actual or real glucose value(s) refers to electrical current reading(s) and/or calibrated current reading(s) that readily track with actual blood glucose level(s) (for example as monitored via a blood glucose test meter). It may be further understood that the first sensor has already been calibrated prior to initiation of the crossover calibration event that relies on method 200.

As one example, the first sensor may have been calibrated using actual blood glucose measurements, for example via a blood glucose test meter/monitor. As another example, the first sensor may have been calibrated using the methodology discussed herein at FIG. 2, in what is referred to herein as serial cross-calibration. Such an example will be elaborated upon in greater detail below.

The electrical current measurement(s) for the first sensor may be continuously recorded, or may be recorded at discrete time points during the first predetermined time period. For example, the electrical current measurement(s) may be recorded at intervals of less than one second, one second, two seconds, 5 seconds, 10 seconds, 20 seconds, 30 seconds, one minute, five minutes, etc., depending on the first determined time period. In some examples, the current measurement(s) may be averaged over such intervals, to generate a smoothed data sample. It may be understood that the first sensor may comprise a glucose sensor, under circumstances where the sensor being calibrated (e.g., a second sensor) also comprises a glucose sensor.

Over the same first determined time period, method 200 at step 220 further includes measuring and recording electrical current value(s) from a second sensor. In certain examples, the electrical current measurement(s) from the second sensor may be recorded at intervals of less than one second, one second, two seconds, 5 seconds, 10 seconds, 20 seconds, 30 seconds, one minute, five minutes, etc., depending on the first determined time period. It may be understood that the first determined time period may comprise a time period that enables a trend in the decay of current from the second sensor to be accurately modeled (e.g., modeled as an exponential decay). The modeling may be done at least in part via a computing device (e.g., analyte sensor computing device 105 at FIG. 1) that retrieves the electrical current measurement(s) from each of the first sensor and the second sensor.

It may be understood that once the decay current can be modeled it may not be necessary to collect additional time points. In other words, the first determined time period may comprise a variable time period. In some examples, this may take up to 60 minutes to ensure there is sufficient information or data to establish and model a trend. This may be at least partially driven by one or more of a rate at which the signal of the second sensor is changing and a rate of glucose level change in the subject. For example, if the signal is stabilizing quickly and the subject's glucose level is not changing very fast, then the first determined time period could be very short. If, on the other hand, the stabilization occurs with a very steep process and if the person's glucose is also rapidly changing, then this first determined time period could be extended up to one or two hours. As a more specific example, if the glucose level in subject is changing very little, as little as 1 to 3 minutes may be sufficient to establish a trend. On the other hand, if glucose value(s) are changing significantly, 15 to 20 minutes may be needed. Longer times are contemplated in some circumstances (e.g., 60 minutes to 2 hours). However, typically 20-30 minutes (and not longer times) may be expected to be needed even under circumstances where the background current is changing dramatically and the glucose concentration is changing rapidly. In embodiments, the second sensor comprises a glucose sensor.

In some examples, to avoid the longer times associated with the first determined time period, it may be desirable to conduct the methodology of FIG. 2 under predetermined conditions. Such predetermined conditions may include when analyte concentration(s) are expected or learned to be stable (e.g., not changing by more than a predetermined threshold change over a predetermined duration of time). With regard to situations where the analyte is glucose, such conditions may comprise situations where fasting glucose level(s) are expected or learned/predicted. For example, based on glucose measurement(s) obtained by one or more glucose sensor(s) over time, trends in glucose concentration(s) throughout a particular time period (e.g., day, hour, etc.) may be established. This information may be relied upon, for example, for prompting the user to insert the second sensor. In other examples, a user may understand that fasting glucose level(s) may be expected at particular times (e.g., upon waking in the morning). Those particular times may be preferred for insertion of the second sensor to avoid situations where glucose value(s) are rapidly changing.

Responsive to the electrical current value(s) being recorded from each of the first sensor and the second sensor over the first determined time period at step 220, method 200 proceeds to 230. At 230, method 200 includes generating glucose value(s) for the first sensor by relying at least in part on the electrical current measurement from the first sensor. While step 230 is depicted as following conclusion of the recording of electrical current measurements of the first sensor, it may be understood that in other examples, step 230 may be carried out concurrently while electrical current measurement(s) are being recorded from the first sensor, provided that enough data has been collected to make a determination of glucose value(s) from the data collected. More specifically, in certain embodiments, glucose value(s) for the first sensor are generated between 5 seconds and 60 seconds during the first time period. Typically this first time period last between about 1 minute and 60 minutes, although this is dictated by the ability of the signal decay of a second sensor (to sensor to be calibrated) to be modeled.

Proceeding to 240, method 200 includes predicting or modeling a background current drop for the second sensor as a function of time over a second period of time. The second period of time may immediately follow the first period of time. In some examples, the second period of time may have some amount of overlap with the first period of time. As one example, the background current drop may be predicted based on a model of an exponential drop. Specifically, it may be understood that the measured current value(s) from the second sensor comprise a total current that is made up of a non-glucose signal, or background current, plus any glucose-specific signal. The data generated during the first determined time period (including one or more of the current value(s) recorded from the first sensor, the glucose value(s) generated for the first sensor, and the current value(s) recorded from the second sensor) may enable a determination of a rate of change of the non-glucose signal. The background current drops can be modeled to establish a pattern. In some examples, the drop may be modeled as an exponential decay that levels out to a linear decay at around a particular time (e.g., 5-7 hours, 6 hours, 12 hours, etc.) after initial insertion of the second sensor. In another example, the drop may be modeled by a power function, structured as $f(x)=ax^{0.5}$. It may be understood that these power functions and exponential functions are not exhaustive, as other models may be used to model specific drops. As discussed above and which will be discussed in further detail below, in some examples, more than one (e.g., 2, or 3) background current drop may be predicted. In such an example, a first background current prediction may comprise a background current drop that levels out to the linear decay around a particular time (e.g., 5-7 hours, 6 hours, 12 hours, etc.). A second background current prediction may be based off historical background current data collected and determined based off one or more previous sensor wear times, for a same type of sensor and the same subject. This second background prediction may extend to an entire wear time of the second sensor, elaborated in greater detail below.

Proceeding to 250, the predicted current drop for the second sensor (which as discussed pertains to the background, or non-glucose driven current) as a function of time is subtracted from the measured current for the second sensor over the second period of time. Accordingly, at 250, method 200 includes measuring current, or in other words continuing to measure current from the second sensor over the second period of time. As mentioned, it may be understood that the first period of time and the second period of time may have some degree of overlap. In certain embodiments, the predicted current drop may be subtracted from the measured current for the second sensor from about the time of insertion until about 12 hours after insertion to even up to 7 days after insertion or substantially longer (e.g., out to 30 days or more of sensor lifetime) under circumstances where historical data from the same subject using a same type of sensor can be used to model background change (e.g., second background current) and current sensitivity changes associated with the second sensor. In certain embodiments, the first predicted current drop may be subtracted from the measured current for the second sensor from about the time of insertion until about 12 hours after insertion. In certain embodiments, the first predicted current drop may be subtracted from about the time of insertion until about 8 hours after insertion. In still other examples, the first predicted current drop may be subtracted from about the time of insertion until about 6 hours after insertion. Other examples of greater or lesser durations for which the predicted current drop may be subtracted from the measured current for the second sensor are within the scope of this disclosure. It may be understood that performing the subtraction procedure as discussed may provide an indication of a contribution of the glucose-specific current change to the measured current for the second sensor.

In certain embodiments, as discussed, the method further includes predicting the second background current (e.g., a current drop and/or rise) for a third time period beginning at least 12 hours, or at least 24 hours after insertion and applying the current prediction from one or more previous sensor wear times comprising the third time period to the sensitivity and the background current. In certain embodiments, the third time period is between about 1-2 days and 30 days after insertion of the second sensor. The second background current may be understood to be able to be predicted based off information or data obtained via the first sensor (or any number of previously worn sensor(s) of the same type by the same subject) that is related to how the second sensor will likely respond in the subject over time. As an example, there may be a protein coating that starts to impact sensor operation beginning on the fifth day of sensor wear time, and which continues until about the tenth day of sensor wear time for a particular subject. This pattern (e.g., a sensor sensitivity change of 25%), which may be learned from the first sensor and/or any number of prior worn sensors for the same subject, may be stored (e.g., at database 180 at FIG. 1, at the analyte sensor itself, and/or at the analyte sensor computational device 105 at FIG. 1), and retrieved for predicting the second background current. This second background current may similarly be subtracted from the measured current from the second sensor, to provide the indication of the contribution of the glucose-specific current change to the measured current for the second sensor. Such a procedure may reduce a number of subsequent calibrations during a wear time of the second sensor, for example if the second sensor relies on any (e.g., once daily or less) blood glucose calibrations, and/or such a procedure may be beneficial to any sensor that includes a factory calibration system.

Proceeding to step 260, method 200 includes using information from the first sensor (e.g., one or more of the glucose value(s) obtained from the first sensor and the current obtained from the first sensor) to create or generate a conversion operation or algorithm for the second sensor. In this way, the subtracted current obtained by subtracting the background, or non-glucose current from the measured current from the second sensor may be converted to second glucose value(s). In some embodiments, the current value(s) may be subjected to smoothing operations. In an example, the smoothing operations may be a combination of medium filters and Kalman signal smoothing operations. In some examples, the subtracted current may be scaled, for example to the first current, and this scaled or calibrated current for the second sensor may be used to develop the conversion operation. However, in other examples, such a scaling may not occur and instead the conversion operation may be built with regard to the subtracted current so that the subtracted current can readily be converted to the second glucose value(s). Thus, at step 260, it may be understood that analyte values have been determined for the first sensor as a function of measured current from the first sensor. Furthermore, the measured current from the second sensor has been subtracted from the background current determined for the second sensor. As such, at 260, method 200 includes building or creating the conversion operation or algorithm that includes glucose conversion terms for the second sensor. Such a conversion operation may be based on one or more of the first current measured from the first sensor, the known glucose value(s) from the first sensor and their relationship to the first current, and the subtracted current as determined by subtracting the background current for the second sensor from the second sensor measured current, as discussed.

In an embodiment, a model of glucose levels (e.g., pattern of glucose level changes learned over time) may be constructed from a history of the individual into which the sensor is being inserted, and this information may be incorporated into the algorithm. The pattern of glucose level change(s) may in some examples be relied upon to predict current and/or future glucose level(s), and such information may be incorporated into the algorithm to improve accuracy and performance of the second sensor. Such information may be stored at a database (e.g., database 180 at FIG. 1). As a representative example, if a motion artifact were to occur while the subject is wearing the second sensor, and such a motion artifact has already been determined as such based on historical data, then the motion artifact may be flagged upon detection, which may prompt a request to check blood glucose values before acting on a glucose reading (e.g., before providing instructions to a subject or insulin delivery system regarding amount of insulin to administer). In other words, it may be learned (e.g., machine learning, deep learning) based on the historical data that the subject's blood glucose is not expected to change as fast or by as much as, for example, a current change induced at the second sensor due to a particular motion artifact. By recognizing the motion-induced artifact prior to acting on a glucose reading stemming from the motion artifact-induced current at the second sensor, instructions that are not relevant to a current biological state may be avoided.

Furthermore, at least some extent of the initial measured current from the second sensor (e.g., day one changes) may be related to biological processes underlying the skin normalizing to the individual. While such a process may differ dramatically between different individuals, the process may have a high likelihood of being quite consistent for a particular individual. Accordingly, in some examples an established or learned pattern of changes (e.g., predictable changes that pertain to the second sensor current changes related to background signal) may be stored, for example at the database (e.g., database 180 at FIG. 1). This established pattern of initial day one changes for that individual may be accessed either from the database or from a profile that has been stored, for example, on the analyte sensor computing device (e.g., analyte sensor computing device 105 at FIG. 1). Other components of the non-glucose related signal may be based on modeling that is related to a rate of change of the non-glucose signal over the time the two sensors are generating data at the same time. In embodiments, part of the calibration may be based on establishing a conversion factor for the signal that remains after the changes in signal, e.g. current value(s) that are not due to changes in glucose have been removed or modeled out. In some examples, this conversion factor may include some level of individual modeling based on a determined rate of deposition of protein on the outside of the sensor and how that changes the response of the sensor to the glucose that it comes into contact with. In some examples, such information may be individual-specific, and may be similarly stored at the database or otherwise associated with a user profile, such that the information can be incorporated into the modeling (for example used at least in part to establish the conversion factor). This conversion factor can also additionally or alternatively include historical factors based on the specific individual's characteristics such as daily glucose excursion profile, daily sensitivity and background current averages or activity level that would have been observed on the same individual with the second sensor. This calibration can be used to convert the net current generated at the second sensor surface to a blood glucose equivalent glucose value(s). Thus, discussed herein, it may be understood that the sensors that are inserted into the skin measure interstitial glucose levels, but the cross calibration methodology used ties the interstitial measurements to blood glucose calibrations (e.g., at least the first sensor is calibrated based on blood glucose samples obtained from a blood glucose test meter). Thus, the analyte values (also referred to herein as glucose values) measured by the interstitially placed sensors may be understood to comprise interstitial values that correspond to blood equivalent values (e.g., blood equivalent glucose values).

Based on the conversion operation developed at 260, at step 270 glucose value(s) are generated for the second sensor. In embodiments, several steps may be involved in the conversion of current value(s) from a sensor to glucose value(s), for example several signal processing steps. In embodiments, a spike detection step which looks for spikes in the current data that could be related to motion artifacts may be relied on. If these are detected then the data may not be used to create a new glucose value, as they can be removed from the calculation. After removal of spike artifacts the smoothed current values can be filtered to create the best quality signal possible. The filtering steps may include one or more of passing through a medium filter, a Kalman filter, or other relevant filter. The glucose value(s) generated can be displayed, for example at the analyte sensor computing device (e.g., analyte sensor computing device 105 at FIG. 1), exported to the database (e.g., database 180 at FIG. 1), and/or communicated to one or more other networked devices (e.g., networked devices 110 at FIG. 1), etc. Method 200 may then end.

It may be understood that the cross-calibration methodology of FIG. 2 may enable serial cross-calibration of a plurality of sensors over time. Specifically, as an example, just a first sensor, when inserted, may have to be calibrated by an external means including but not limited to actual blood glucose measurements (e.g., via a blood glucose test meter). Then, following that initial calibration procedure, any number of subsequent sensor insertion events may rely on the cross-calibration methodology of FIG. 2, thereby alleviating a subject from having to perform calibration routines that involve the obtaining of actual blood glucose measurements. This may improve customer/user satisfaction, and reduce opportunity for infection or other adverse biological responses associated with repeated use of glucose test meters. Furthermore, overall costs may be reduced, as the reliance on actual blood glucose test results may be reduced or essentially avoided following the first sensor calibration. As a specific example, following calibration of a first sensor via the use of actual blood glucose measurements, upon insertion of a second sensor after a period of time the cross-calibration procedure of FIG. 2 may be used to calibrate the second sensor. The first sensor may then be removed from the subject, and the second sensor may be relied upon for blood glucose determinations. After another period of time, a third sensor may be inserted into the subject, and again, the cross-calibration procedure of FIG. 2 may be used to calibrate the third sensor based off of the second sensor. The second sensor may then be removed, and the third sensor may be relied upon for blood glucose determinations. As mentioned, this process may be repeated any number of times.

To improve accuracy of blood glucose determinations based on the cross-calibration methodology, it may be desirable to confirm that the cross-calibration methodology has been successful (e.g., that the second sensor is calibrated to a level of accuracy or sensitivity expected or desired). Discussed herein, sensitivity may be understood to relate to a ratio of current to analyte concentration. For example, it may be desirable to ensure that, following the cross-calibration procedure, a second sensor that has been recently calibrated exhibits expected behavior in terms of glucose determinations and sensitivity that align with previous glucose determinations/sensitivity from a first sensor used in the cross-calibration process. Additionally, it may be desirable to ensure the second sensor is operating as expected or desired prior to a subject removing the first sensor. For example, under conditions where the first sensor is working as desired, but for some reason the second sensor is not, then it may be advantageous to continue relying on the first sensor for glucose determinations until another sensor can be properly calibrated for use.

Figure 3:
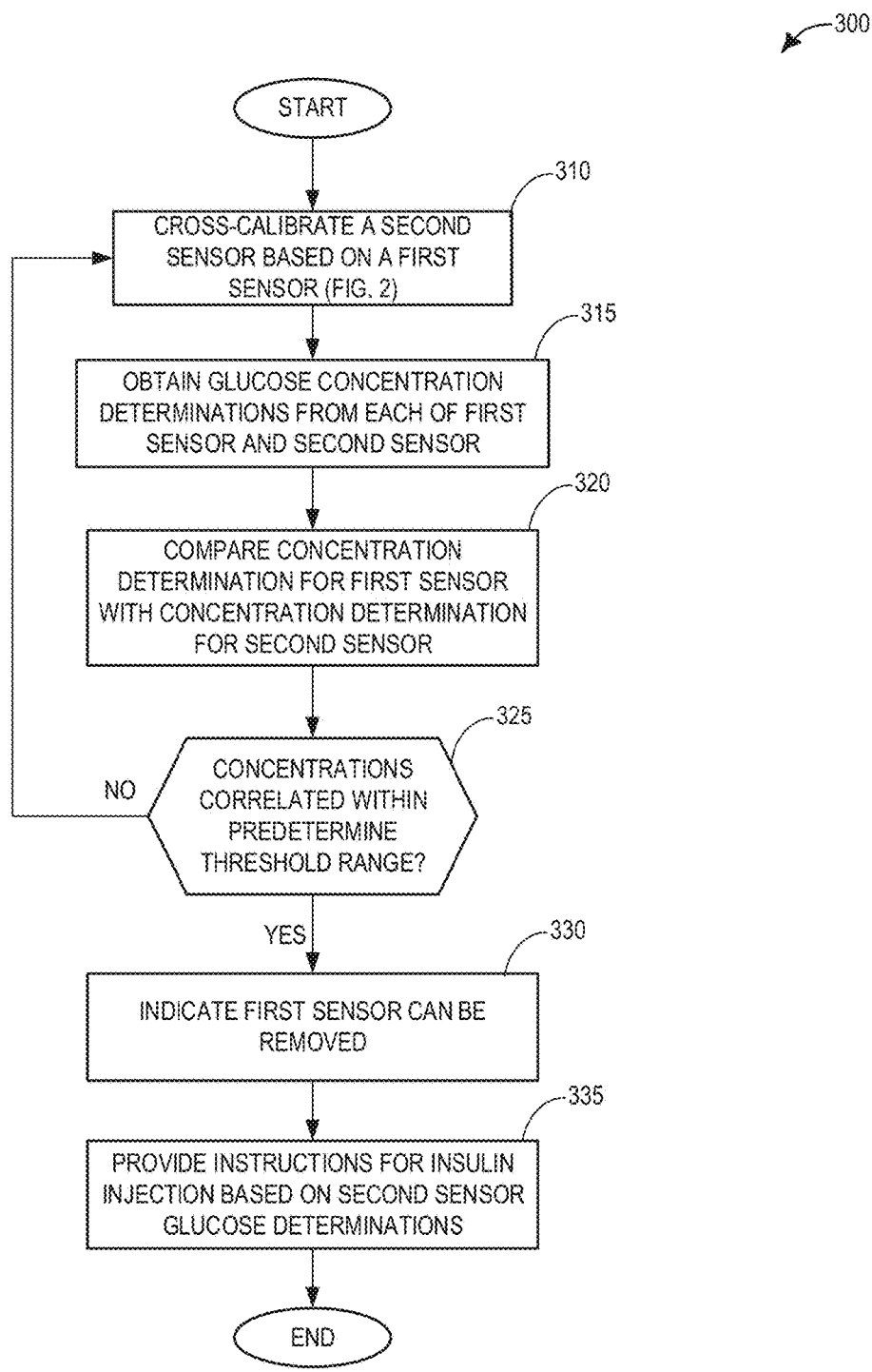
FIG. 3 is a flow chart showing an example method for determining whether a sensor has effectively been cross calibrated via the methodology of FIG. 2.

Accordingly, turning now to FIG. 3, an example method 300 is shown for determining whether a cross-calibration procedure conducted via the method of FIG. 2 results in a newly inserted sensor having been properly calibrated (e.g., calibrated as expected or desired). Method 300 may comprise a computer implemented method, and may comprise software instructions stored on a non-transitory computer readable medium that, when executed by a processor, cause the processor to perform the instructions set forth by the steps of method 300.

Method 300 begins at 310, and includes performing a cross-calibration procedure as discussed with regard to FIG. 2, for a second sensor that has been inserted into a subject who already has a previously calibrated first sensor inserted. Following cross-calibration, method 300 proceeds to 315. At 315, method 300 includes obtaining glucose concentration determination(s) from each of the first sensor and the second sensor. Step 315 may comprise obtaining one or more glucose determinations from each of the first and the second sensor. As one example, a plurality of glucose determinations may be obtained for each of the first and the second sensor, over a predetermined period of time following the cross-calibration procedure (or even at some point during the cross calibration procedure). In some examples, three different measurements for each of the first sensor and the second sensor may be obtained over the predetermined period of time (e.g., 30 seconds, 1 minute, 2 minutes, 5 minutes, etc.). In other examples, any number of measurements greater than three may be obtained over the predetermined time period.

With the glucose concentration determinations obtained for each of the first and the second sensor, method 300 proceeds to 320. At 320, method 300 includes comparing the glucose concentration determinations. As one example, a fitting procedure (e.g., linear fit, method of least squares, etc.) may be performed on the data obtained for each sensor to establish trend lines for each of the sensors. This may enable a first trend and a second trend to be established for each of the first sensor and the second sensor. The fits for each set of data may then be compared to determine whether the second sensor is producing glucose concentration determinations that align or correlate with the glucose concentration determinations obtained via the first sensor. If the trend for the second sensor does not overlap with the trend for the first sensor within a predetermined threshold range, then it may be indicated that the glucose concentration determinations made via the second sensor are not correlated with the glucose concentration determinations made via the first sensor. Alternatively, if the trend for the second sensor aligns with the trend for the first sensor within the predetermined threshold range, then it may be indicated that the glucose concentration determinations made via the second sensor are correlated with the glucose concentration determinations made via the first sensor.

Accordingly, responsive to an indication that the second sensor glucose concentration determinations align or are correlated with the glucose concentration determinations made via the first sensor, method 300 proceeds to 330. At 330, method 300 includes providing an indication that the first sensor can be removed. Such an indication may be provided, as an example, digitally via a display screen associated with the analyte sensor computing device (e.g., analyte sensor computing device 105 at FIG. 1). Additionally or alternatively, the indication may be provided via an audible alert, which in some examples may stem from either the analyte sensor computing device or the first sensor itself. Additionally or alternatively, some other means (e.g., visual alert such as an LED or other light-based alert) may be used to communicate to the user that the first sensor can be removed. For example, the alert may comprise a text-based message sent to an application on a phone of the user, an email, etc.

Proceeding to 335, method 300 includes providing instructions for insulin injection based on second sensor glucose determinations over time until yet another sensor is inserted into the subject. It may be understood that this step may be optional in some examples where glucose determinations are not associated with either open-loop or closed-loop insulin injection steps. For example, a user may in some examples desire to monitor glucose levels over time without also performing insulin injection steps based on the data obtained. However, in other examples where insulin injection steps occur based on the glucose determinations, then step 335 may be included. As one example, the instructions provided at 335 may include instructions for viewing by a user, for example via a display screen associated with the analyte sensor computing device (e.g., analyte sensor computing device 105 at FIG. 1). If the instructions are simply provided for viewing by a user, then it may be understood that the insulin injection relates to an open-loop insulin injection methodology, as it is up to the user to perform the procedure of insulin injection provided via the instructions.

Alternatively, the instructions provided at 335 may comprise instructions sent to an insulin delivery unit (e.g., insulin delivery unit 170 at FIG. 1). Such an example may be understood to comprise a closed-loop insulin injection methodology. Specifically, based on the glucose concentrations determined, appropriate instructions may be provided to the insulin delivery unit such that a determined amount of insulin is thereby injected automatically, without user input.

It may be understood that method 300 may end responsive to an indication that the first sensor can be removed and/or responsive to the second sensor being used to provide glucose concentration determinations, which in some examples may additionally include such concentration determination being relied upon for providing instructions pertaining to insulin injection.

Returning to 325, in an example where the glucose concentration determinations for the second sensor are not indicated to align or correlate with the glucose determinations obtained via the first sensor, method 300 may continue to be conducted until it is indicated that concentrations are correlated within the predetermined threshold range at 225. As depicted, in some examples, continuing to conduct method 300 may additionally include repeating the cross calibration procedure of FIG. 2 before proceeding with the methodology of FIG. 3. However, in other examples, the same cross calibration may be used, and additional glucose concentrations may simply be determined for each of the first sensor and the second sensor, such that the comparison at step 320 may be repeated. Once it is indicated that the concentrations are correlated within the predetermined threshold range at 325, method 300 may proceed to 330 as discussed above. While not explicitly illustrated, in some examples where an affirmative result is not returned at step 325 after a predetermined number of attempts, mitigating action may be taken to calibrate the second sensor in an additional or alternative way. As one example, the method may include a request that the second sensor be calibrated based on a blood glucose test measurement or measurements. As another example, the method may include a request that the first sensor be calibrated based on such a blood glucose test measurement or measurements, to ensure the first sensor is functioning as desired or expected. Once it has been confirmed that the first sensor is functioning as desired or expected, then the methodology of FIG. 3 may once again be relied upon for determining when the second sensor has effectively been calibrated at step 325.

Figure 4:
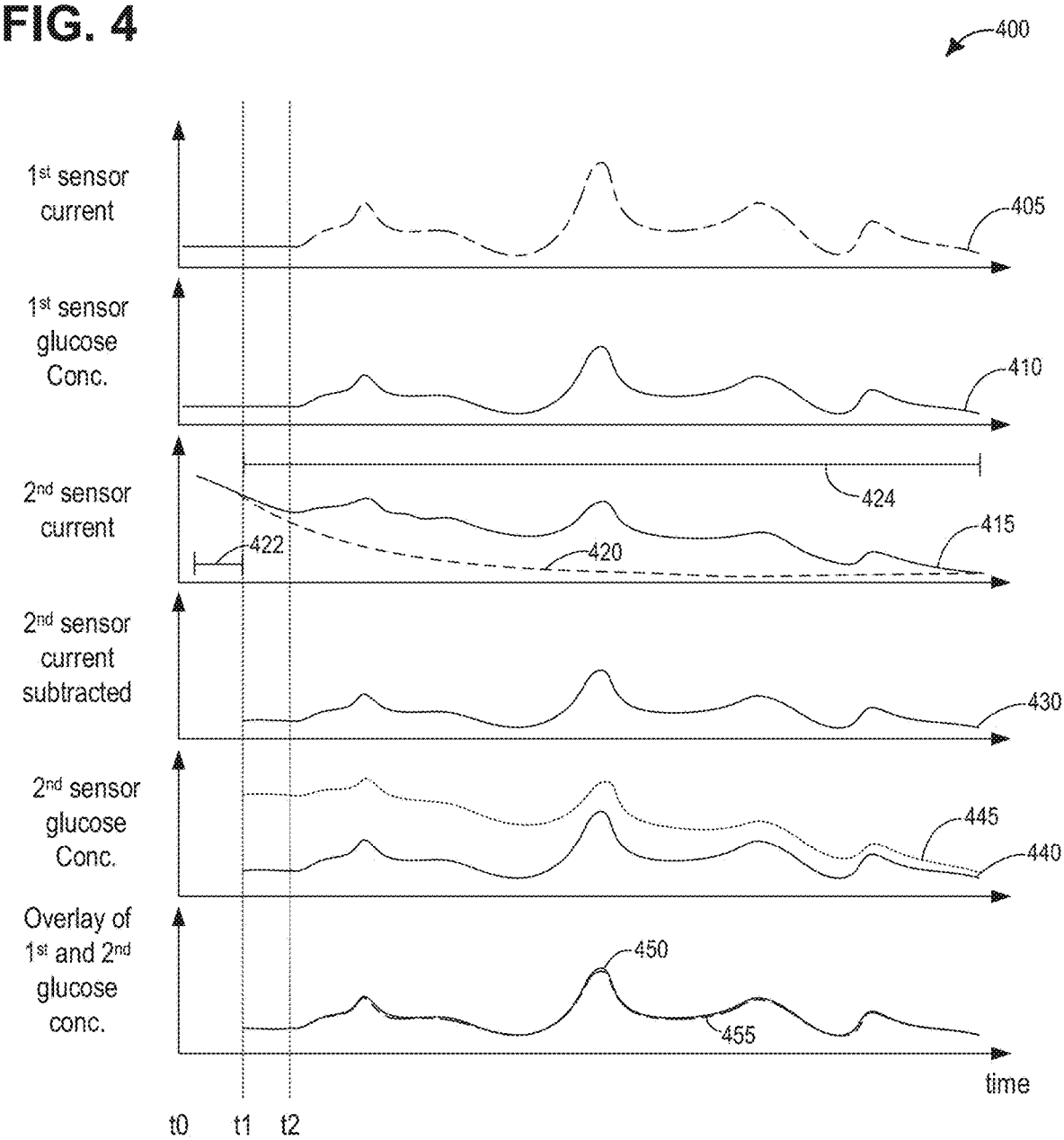
FIG. 4 is a prophetic example timeline illustrating the cross-calibration methodology of FIG. 2.

Turning now to FIG. 4, a prophetic example timeline 400 is shown, illustrating how the cross calibration methodology of FIG. 2 is conducted. All plots at FIG. 4 are depicted with respect to time (x-axis) and accordingly, may be understood to occur as a function of time. Timeline 400 includes plot 405, indicating raw current recorded from a first sensor, over time. In this example timeline, it may be understood that the first sensor has been implanted in a subject for approximately 12 days, however in other examples longer times are contemplated (e.g., up to 30 days). Timeline 400 further includes plot 410, indicating glucose concentration over time, as determined via converting the raw current from the first sensor (plot 405) into glucose values. Timeline 400 further includes plot 415, indicating raw current recorded from a second sensor, over time. It may be understood that for this example timeline, the second sensor has been inserted into the subject near time t0. Timeline 400 further includes plot 420, indicating a predicted background current associated with the second sensor, over time. Line 422 represents the first time duration (refer to step 220 at FIG. 2) and line 424 represents the second time duration (refer to step 250 at FIG. 2). Timeline 400 further includes plot 430, indicating a subtracted second sensor current obtained by subtracting the predicted background current (plot 420) from the raw second sensor current (plot 415), over time. Timeline 400 further includes plot 440, indicating glucose concentration as measured by the second sensor, over time, as determined via converting the subtracted second sensor current (plot 430) into glucose values. Timeline 400 further includes plot 445, representing glucose values which otherwise may have been obtained from the second sensor if the cross-calibration process were not conducted. Timeline 400 further includes plot 450, indicating the same glucose values as plot 440 (glucose values obtained from the cross calibrated second sensor), overlaid with plot 455, indicating the same glucose values as plot 405 (glucose values obtained from the first sensor, where the first sensor was already previously calibrated prior to time t0).

At time t0, the cross calibration process is initiated. A timeframe spanning time t0 and t1 comprises the first time duration in this example timeline 400. During the first time duration, current is measured from the first sensor (plot 405) and second sensor (plot 415). Furthermore, glucose values are obtained for the first sensor (refer to plot 410) based on the current recorded from the first sensor.

The first time duration comprises a variable time duration, which may be understood to be based on an ability to model or predict the background current. In this example timeline, glucose values are not changing significantly during the first time duration (refer to plot 410), and thus it may be understood that the time between time t0 and t1 represents just a few minutes. Specifically, as mentioned above, the first time duration may be shorter under circumstances where glucose levels are not rapidly changing, because of the ability to readily model the decay current associated with the second sensor. At time t1, the background current is predicted (plot 420), based at least in part on the decay of the raw current for the first sensor (plot 415) during the first time duration. It may be understood that the prediction of the background current may take into account other factors including, but not limited to, one or more of the raw current measured via the first sensor (plot 405), the glucose values obtained from the first sensor (refer to plot 410), and historical data retrieved, for example, from a database (e.g., database 180 at FIG. 1) or other data storage device that stores data previously obtained from sensors worn by the same subject. In some examples, a pattern of background current decay may be learned over time (e.g., via machine learning algorithms or deep learning algorithms) and this pattern may be recalled or retrieved for assisting in predicting the background current. The background current is predicted for a second time duration (line 424) extending past the first time duration, as depicted.

Between time t0 and t1, glucose levels in the subject stay relatively steady (refer to plot 410), and thus the raw current from the second sensor (plot 415) approximately tracks with the predicted background current (plot 420). At time t2, glucose levels in the subject begin to change (plot 410). As a result, measured current from the second sensor (plot 415) deviates from the predicted background current (plot 420). During the second duration, the predicted background current (plot 420) is subtracted from the second sensor current (plot 415), to yield a subtracted second sensor current (plot 430). Based on one or more of the measured current from the first sensor (plot 405), the glucose values obtained from the first sensor (plot 410), and the subtracted sensor current (plot 430), a conversion operation or algorithm is generated for producing glucose values for the second sensor. Based on the conversion algorithm, second sensor glucose values (plot 440) are obtained. For reference, plot 445 illustrates second sensor glucose values that may otherwise have been obtained if the cross calibration procedure were not conducted for the second sensor. Specifically, while the background current is changing (e.g., decaying) over time, the second sensor may not be accurate if the raw current is relied upon for inferring glucose values, as opposed to relying on the subtracted second sensor current. Plot 450 represents the same glucose values as plot 440, and plot 455 represents the same glucose values as plot 405, to illustrate that the cross calibration methodology results in the second sensor accurately reporting on glucose values similarly to the first sensor. Once it is established that the second sensor is operating as expected or desired, the first sensor may be removed. For example, as discussed above with regard to the methodology of FIG. 3, and in particular with regard to step 325 of method 300, the glucose values as determined via the first sensor may be compared to glucose values as determined via the second sensor, and responsive to an indication that the values are correlated within the predetermined threshold range, it may be indicated that the first sensor may be removed. In a case where the glucose values determined via the first sensor are not indicated to be correlated with the glucose values determined via the second sensor, then the method may continue to loop as discussed above, until an affirmative response (e.g., yes) is returned at step 325 of method 300, enabling the subject to remove the first sensor.

While not explicitly illustrated at FIG. 4, it may be understood that in some examples a second background current may be obtained, for example at a predetermined time since the second sensor was inserted (e.g., 12-24 hours post second sensor insertion). The second background current may be modeled based on data retrieved from any number of other previously worn sensor(s), which may include the first sensor, provided the other previously worn sensor(s) are of the same type as the second sensor, and that the subject is the same between the previously worn sensor(s) and the second sensor. The second background current may be modeled out to an entirety of the wear time for the second sensor. For example, the second background current may be modeled out to 15 days or more, 20 days or more, or 25 days or more, or 30 days or more. By modeling the second background current to such lengths of time after the second sensor is inserted, current measured by the second sensor may continue to be subtracted for the lifetime of the second sensor. This may improve accuracy of the second sensor, for example, with respect to the converting of the subtracted current obtained from the second sensor to second sensor glucose values.

It may be understood that the first background current may be subtracted during a first time duration, and that the second background current may be subtracted during a second time duration. Each of the first time duration and the second time duration may be variable. For example, a conversion operation that includes one or more conversion parameters may be built or generated, as discussed, which may be used to convert the subtracted current into second sensor glucose values during each of the first time duration and the second time duration. During the first time duration, responsive to an indication that the conversion operation is effectively and accurately converting the subtracted current into second sensor glucose values, the first time duration may end. Similarly, during the second time duration, responsive to an indication that the conversion operation is effectively and accurately converting the subtracted current into second sensor glucose values, the second time duration may end. Said another way, the first time duration and the second time duration may not comprise predetermined durations of time, but rather, the disclosed processes corresponding to each of the first duration and the second duration may conclude when they are no longer needed. It may be understood that the processes are no longer needed to continue when the conversion parameters for the second sensor and background correction for the second sensor have been correctly established. In some examples, the one or more conversion parameters may be the same for use during the first duration and the second duration, however it may be understood that the one or more conversion parameters may be different, without departing from the scope of this disclosure.

Furthermore, while not explicitly illustrated at FIG. 4, it may be understood that in some examples, the determination of the second sensor glucose values may be based at least in part on analyte sensitivity values determined as a function of time for previously worn sensor(s) (e.g., any number of previously worn sensor(s) provided the sensors are of the same type as the second sensor, and worn by the same subject as the second sensor). The analyte sensitivity values may relate to biological processes that occur over time in a subject in response to a new sensor (e.g., second sensor being inserted). As an example, such a biological process may include protein coating of the newly inserted sensor. Such a process may be quite similar as a function of time with regard to a newly introduced sensor(s), and a conversion factor(s) may be determined such that learned analyte sensitivity changes that reliably occur over time in a particular subject may be applied to newly introduced sensors. In this way, sensitivity for newly introduced sensors may be improved during the time that the newly introduced sensor is worn by the subject (e.g., for an entire lifetime of the sensor).

In this way, accuracy and sensitivity of newly inserted analyte sensors may be improved, particularly in a time period where accuracy and sensitivity would otherwise be degraded due to issues related to changing background currents. By using the cross calibration methodology discussed herein, a newly inserted sensor may readily be calibrated based on another sensor that is already inserted subcutaneously into a subject, thereby avoiding calibration methodology that relies on actual blood measurements.

EXAMPLES

Example 1

Comparison of Cross-Calibration Methodology Versus Calibration Methodology that Relies on Actual Blood Glucose Test Measurements This Example demonstrates that cross-calibration methodology as discussed herein at FIG. 2 is superior in terms of calibration of CGM sensors compared to calibration methodology that relies on actual blood glucose test measurements.

Figure 5:
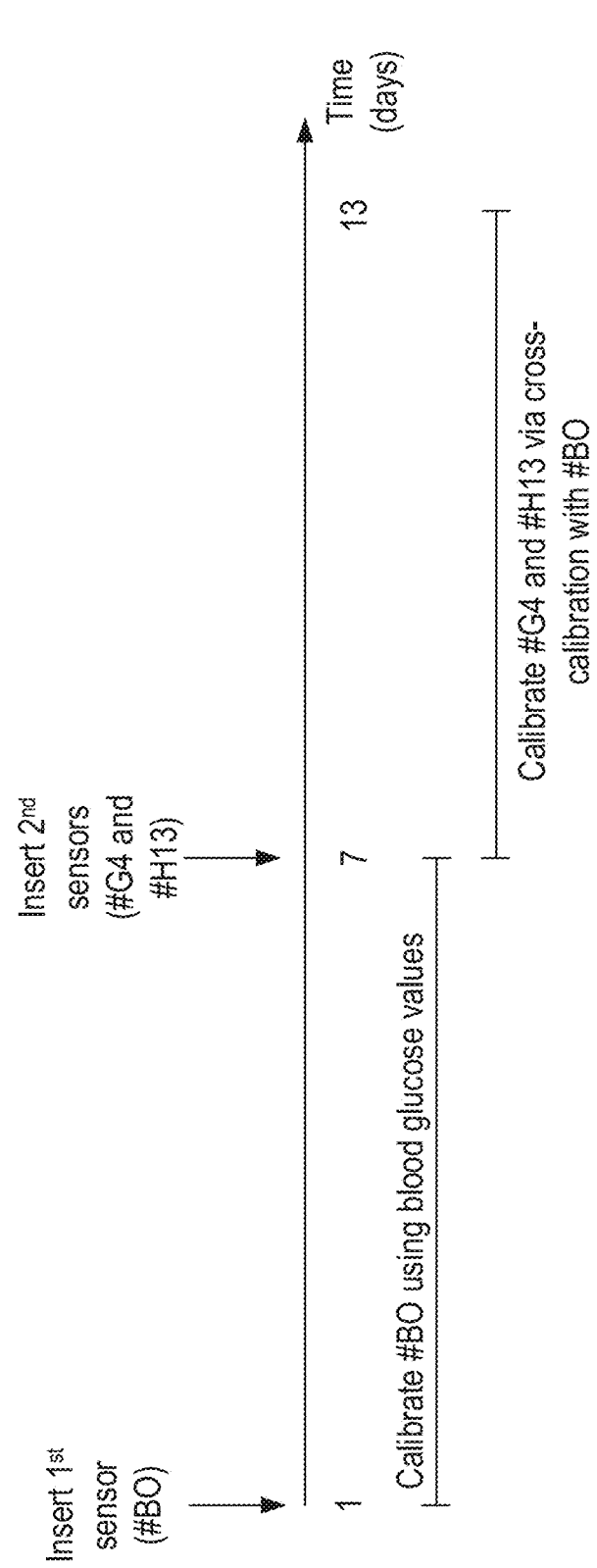
FIG. 5 is a schematic depiction of an experimental procedure conducted to illustrate the effectiveness of the cross-calibration methodology of FIG. 2.

Turning to FIG. 5, depicted is an example timeline 500 for an experimental procedure for testing the cross-calibration methodology discussed above at FIG. 2. Briefly, the procedure included inserting a first CGM sensor (#BO) into a subject at day 1. The first CGM sensor (#BO) was inserted 6 days prior to inserting a second CGM sensor (#G4) and a third CGM sensor (#H13). The first CGM sensor (#BO) was calibrated using blood glucose values obtained via a blood glucose test meter during the days it was worn, prior to insertion of the second and third sensors at day 7. Following insertion of the second (#G4) and third (#H13) sensors, each of the second and third sensors were calibrated using the cross-calibration methodology depicted above at FIG. 2. Specifically, the first sensor (#BO) was relied upon for cross-calibration of each of the second (#G4) and third (#H13) sensors. Data resulting from the experimental procedure depicted at FIG. 5 is depicted at FIGS. 6-8.

Figure 6:
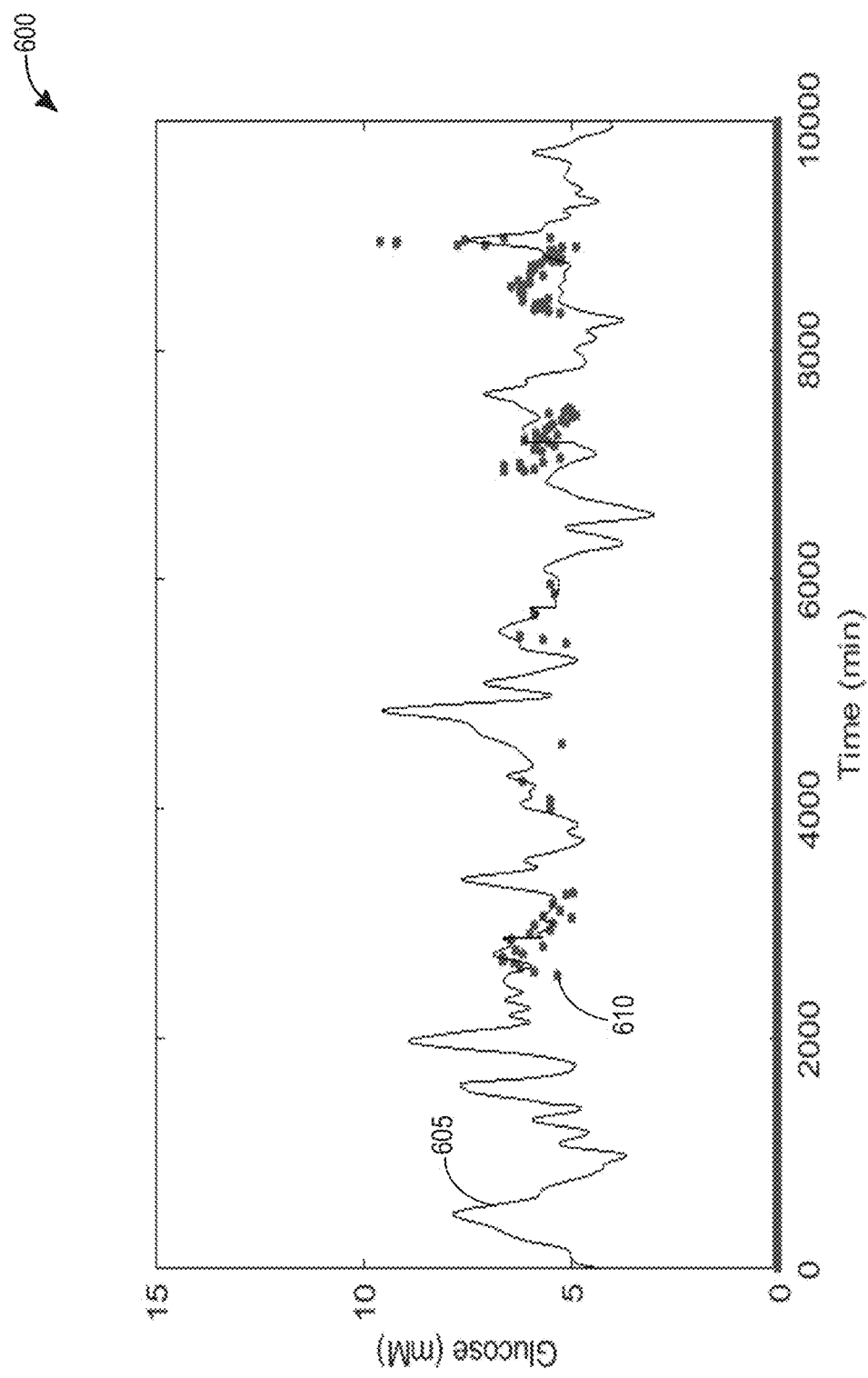
FIG. 6 is a graph showing glucose concentration as determined by a continuous glucose monitor (CGM) with a calibrated analyte sensor (CGM #BO) and as determined by a blood glucose test meter, in accordance with various aspects described herein.

Specifically, FIG. 6 is a graph 600 showing CGM measurements 605 converted to glucose concentration (mM) for the first CGM sensor (#BO), along with a number of actual blood glucose measurements 610, made via the blood glucose test meter. As mentioned, the first sensor was calibrated based on actual blood glucose measurements, and a select number of actual blood glucose measurements 610 are shown to illustrate accuracy of the calibration of the first sensor (#BO).

Figure 7:
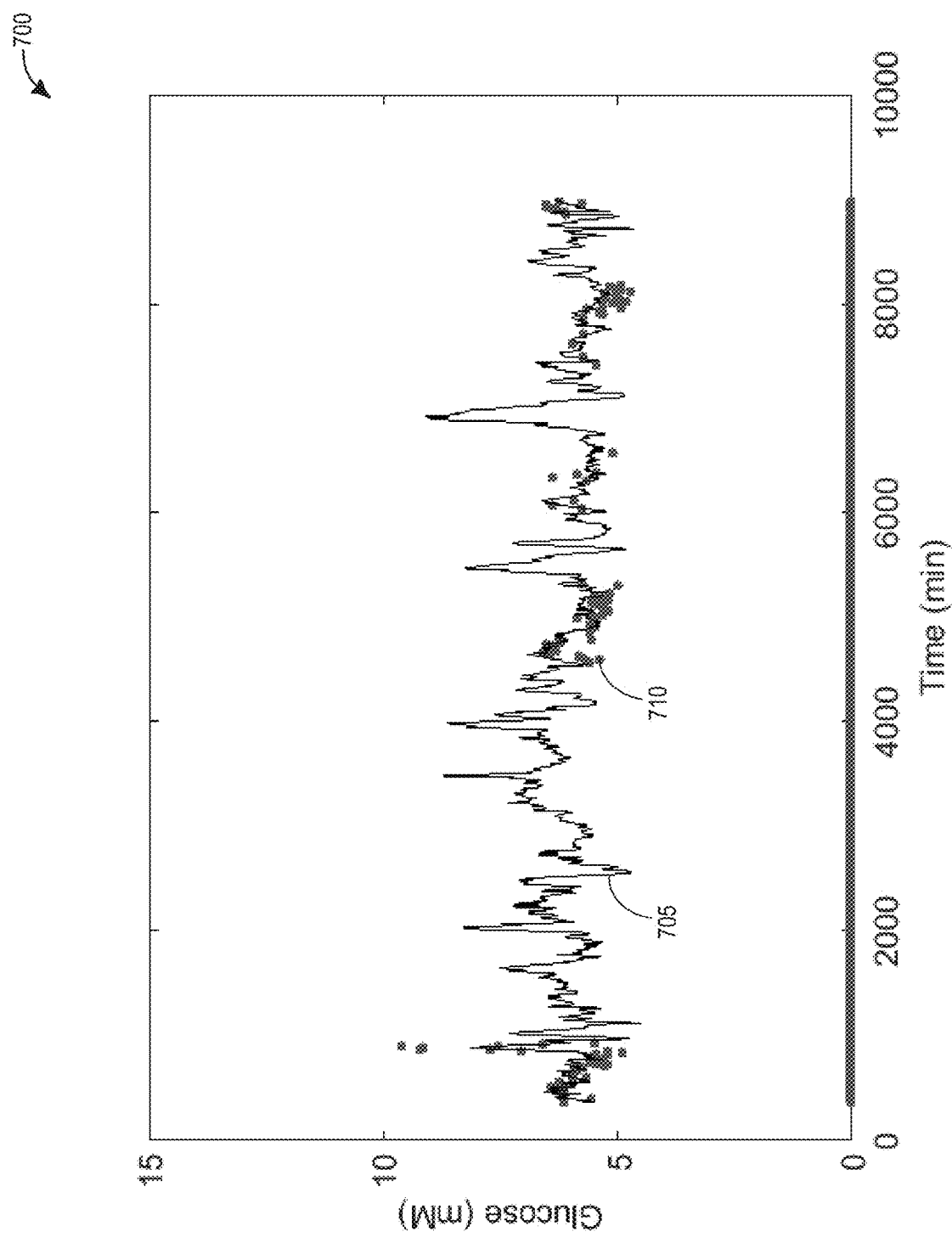
FIG. 7 is a graph showing glucose concentration as determined by a CGM with an analyte sensor (CGM #H13) that has been cross-calibrated to the analyte sensor (CGM #BO) depicted in FIG. 6, and as determined by a blood glucose test meter, in accordance with various aspects described herein.

FIG. 7 is a graph 700 showing CGM measurements 705 converted to glucose concentration (mM) for the second CGM sensor (#G4). The second CGM sensor at FIG. 7 was cross-calibrated via the methodology of FIG. 2 to the first CGM sensor (#BO). Also shown at FIG. 7 are a number of actual blood glucose measurements 710, made via the blood glucose test meter. It may be understood that the actual blood glucose measurements 710 were not used in any way to calibrate the second CGM sensor (#G4), but are shown to illustrate accuracy of the cross-calibration methodology by which the second CGM sensor was calibrated. It may be further understood that time 0 (min) at FIG. 7 represents when the second CGM sensor was inserted into the subject.

Figure 8:
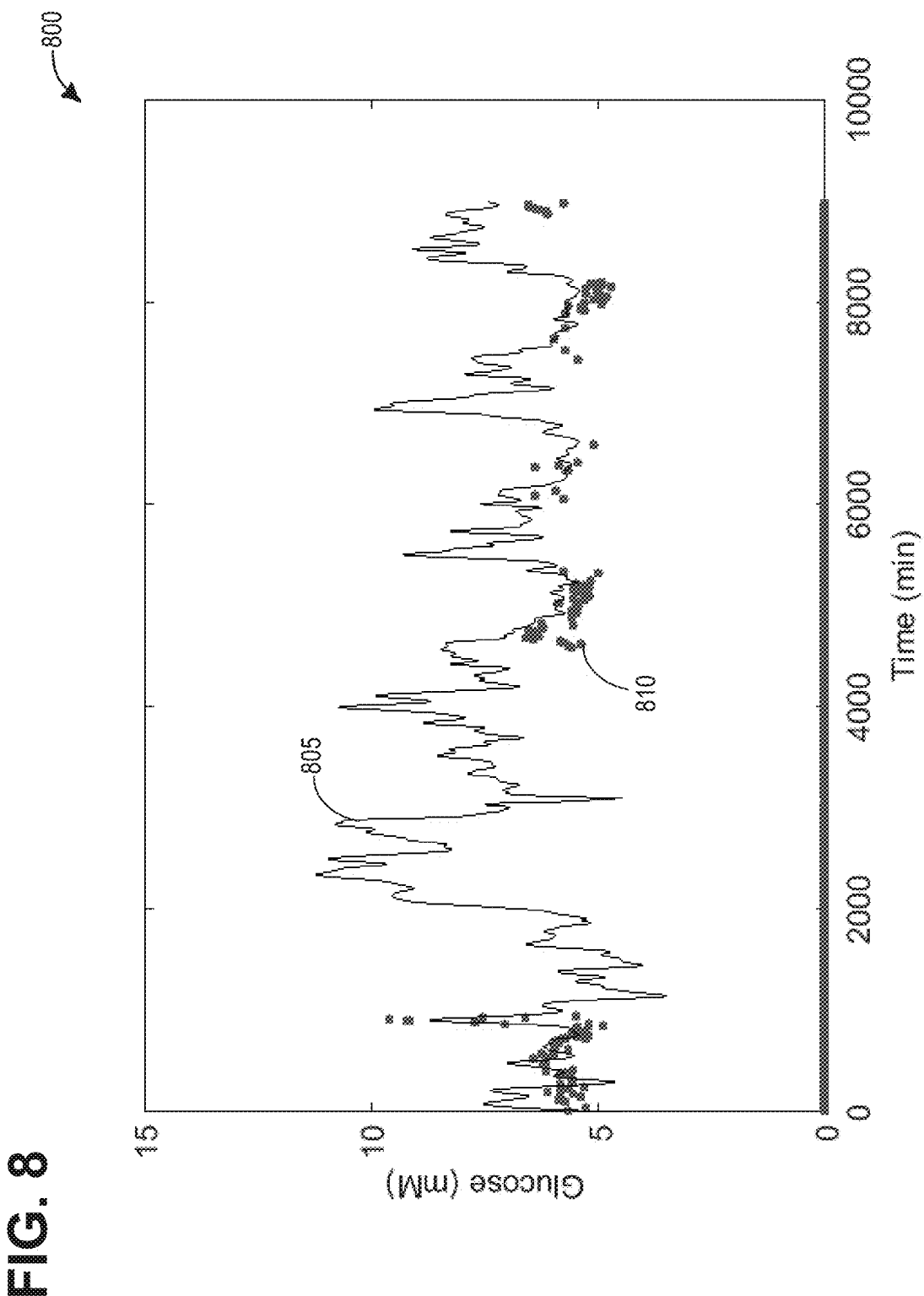
FIG. 8 is a graph showing glucose concentration as determined by a CGM with an analyte sensor (CGM #G4) cross-calibrated to the analyte sensor depicted in FIG. 6 (CGM #BO) and the blood glucose as determined by a blood glucose test meter, in accordance with various aspects described herein.

FIG. 8 is a graph 800 showing CGM measurements 805 converted to glucose concentration (mM) for the third CGM sensor (#H13). The third CGM sensor at FIG. 8 was cross-calibrated via the methodology of FIG. 2 to the first CGM sensor (#BO). Also shown at FIG. 8 are a number of actual blood glucose measurements 810, made via the blood glucose test meter. It may be understood that the actual blood glucose measurements 810 were not used in any way to calibrate the third CGM sensor (#H13), but are shown to illustrate accuracy of the cross-calibration methodology by which the third CGM sensor was calibrated. It may be further understood that time 0 (min) at FIG. 8 represents when the third CGM sensor was inserted into the subject.

With regard to each of FIGS. 7-8, it may be understood that current data and calibrated glucose levels obtained from the first CGM sensor (#BO) were used in the methodology of FIG. 2 as part of the cross-calibration process for each of the second (#G4) and third (#H13) sensors, respectively.

Table 1 represents the results of the accuracy of the cross-calibration process used to calibrate the second (#G4) and third (#H13) CGM sensors compared with the calibration process used for the first CGM sensor (#BO) that relied on actual blood glucose test readings.

TABLE 1

Mean absolute relative deviation analysis

| | MARD (%) | | |
|---|---|---|---|
| Sensor # | Cross-cal. Day 1-7 | Cross-cal. Day 2-7 | Daily re-calibration via blood glucose measurements |
| H13 | 14.3 | 11.4 | 16.0* |
| G4 | 10.6 | 6.1 | 15.7* |

The results depicted at Table 1 show that when a cross-calibration was done on sensor #H13 the overall error of the readings (as expressed as MARD) was 14.3% on day 1 and 11.4% over the remaining 6 days (where day 1 refers to the day the second CGM sensor (#H13) was inserted into the subject. When the same error calculation was done on the first CGM sensor (#G4) the error on day 1 was 10.6% and 6.1% over the remaining six days. The last column represents the results when blood glucose values are used to calibrate the CGM sensor response. These results demonstrate that the crossover calibration method disclosed herein produces superior results over other calibration methodology that relies on actual blood glucose measurements. Specifically, calibration that relies on actual blood glucose measurements would produce results of 16.0% for sensor #H13 and 15.7% for sensor #G4. This analysis demonstrates advantages of the cross-calibration methodology as herein discussed. First, this Example shows that the methodology of cross-calibration provides a better estimation of the NGC and thus, results in much better performance than a calibration process that relies on actual blood glucose test measurements. Second, this Example shows that being able to use multiple glucose values close in proximity provides a better calibration process than does multiple values spread over 7 days.

Example 2

Figure 9A:
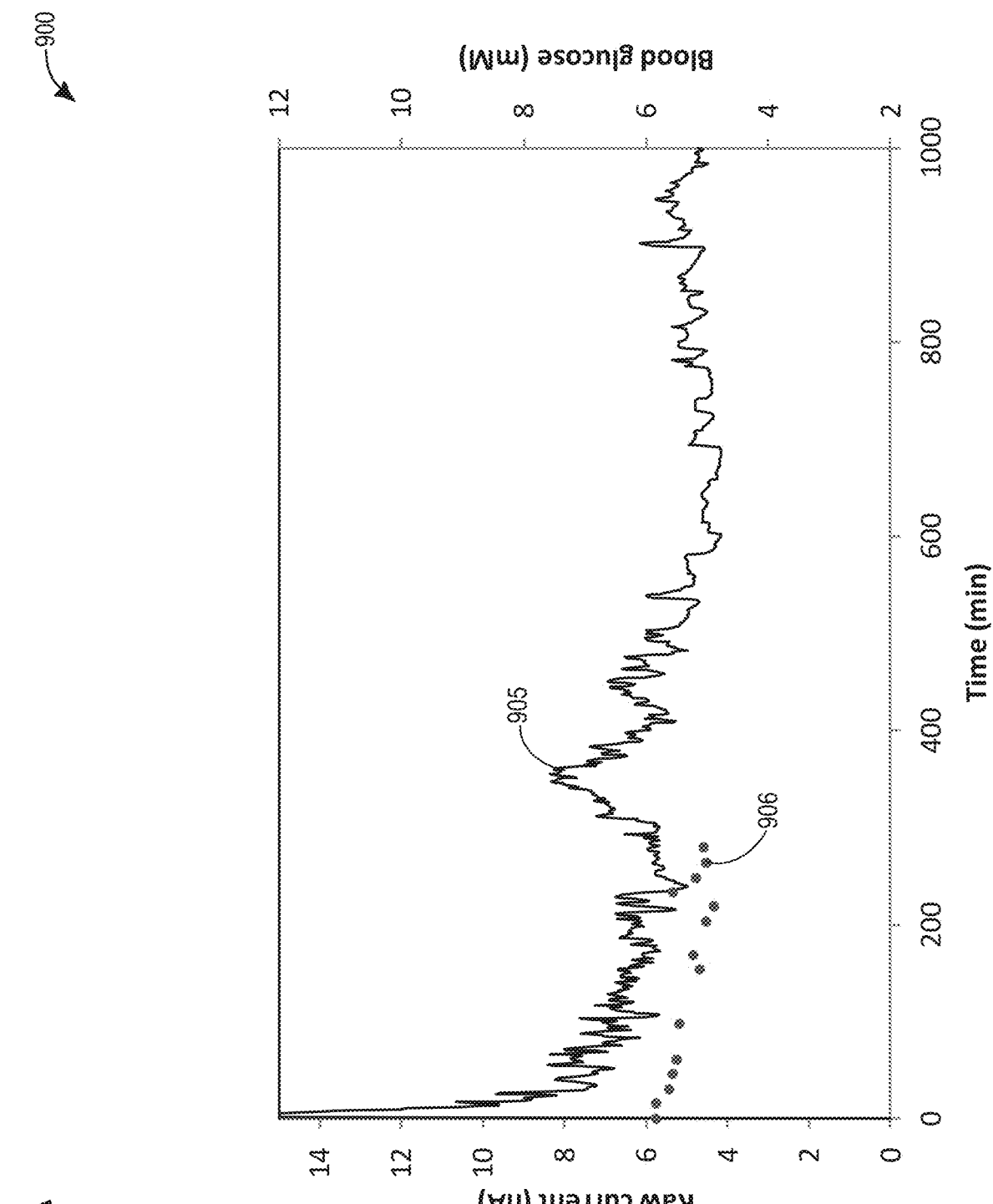
FIG. 9A is a graph showing a raw, uncalibrated analyte sensor signal (line) versus actual blood glucose readings (dots).

Raw Uncalibrated Current Trace and Comparison Between a CGM Sensor Calibrated Via Cross-Calibration Methodology and Actual Blood Glucose Measurements This Example demonstrates that the background current signal for a CGM sensor starts high after insertion and gradually proceeds through an exponential drop, and that by using the methodology of cross-calibration, accurate glucose readings can be produced just following sensor insertion into a subject. Specifically, FIG. 9A is a graph 900 showing an example of raw uncalibrated current (nA) 905 from a CGM sensor inserted into a subject, over time. The time reflects minutes following sensor insertion, and illustrates how the current proceeds to drop over a timeframe spanning approximately 6-12 hours. For reference, also depicted are actual blood glucose values 906, obtained from the same subject from which the CGM sensor is inserted. The discrepancy between raw current and actual blood glucose illustrates a need for correction of the background, or non-glucose, signal that is driving the drift seen in the raw current trace 905.

Figure 9B:
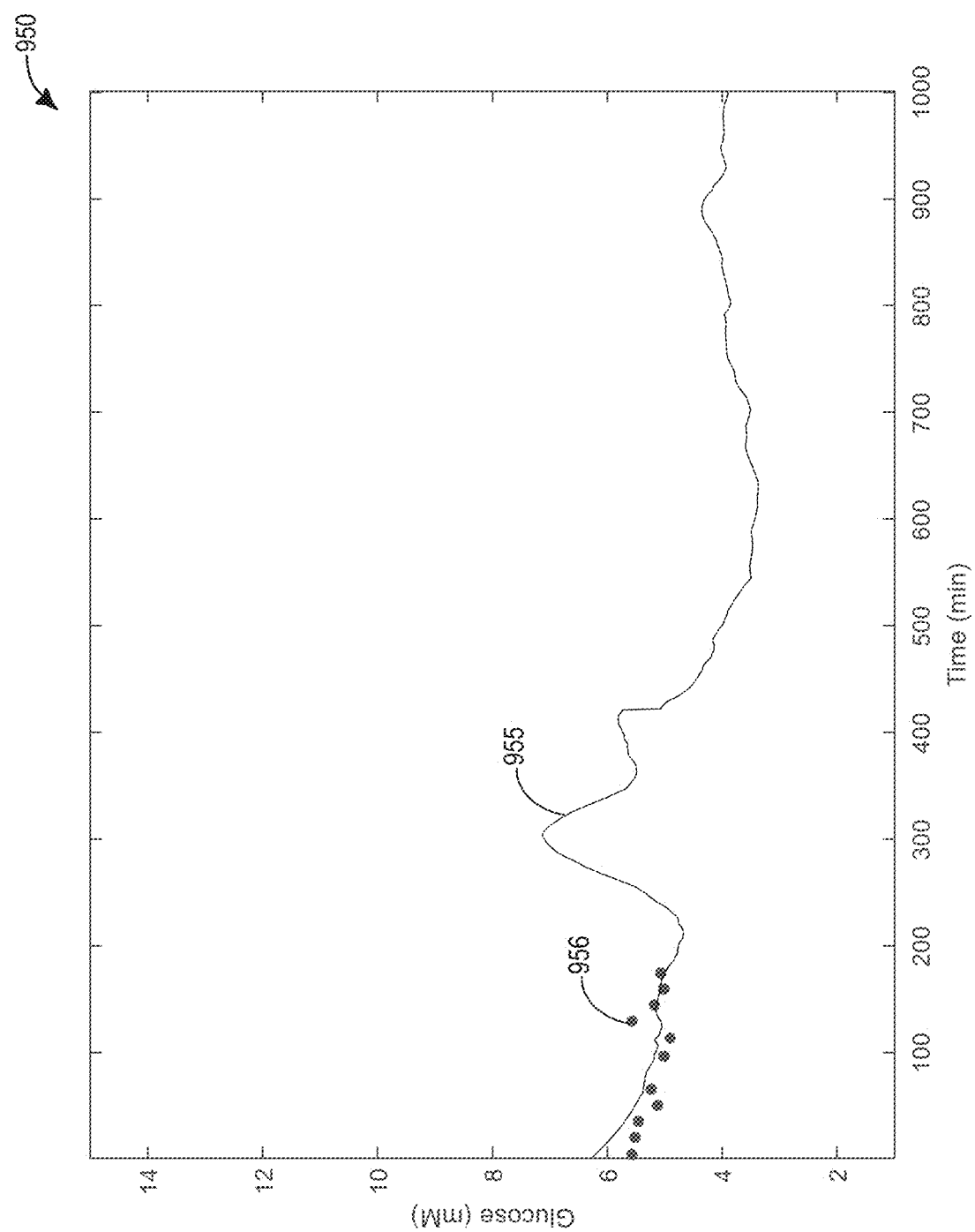
FIG. 9B is a graph showing a calibrated analyte sensor signal (line) versus actual blood glucose readings (dots).

Turning to FIG. 9B, depicted is a graph 950 showing an example of glucose concentration determinations for the CGM sensor discussed at FIG. 9A, inserted into the subject, as a function of time. Specifically, line 955 depicts glucose measurements determined via the CGM sensor discussed at FIG. 9A, and dots 956 represent actual blood glucose measurements obtained via the blood glucose test meter. The CGM sensor was calibrated upon insertion via the cross-calibration methodology. This example illustrates that cross-calibration yields glucose measurements that closely approximate actual glucose measurements as determined via a blood glucose test meter. Said another way, this example illustrates that the cross calibration methodology discussed herein corrects for the discrepancy between raw current trace (line 905 at FIG. 9A) and actual blood glucose values (dots 906 at FIG. 9A and dots 956 at FIG. 9B), to yield CGM-based blood glucose determinations (refer to plot 955 at FIG. 9B) that accurately reflect actual blood glucose determinations (plot 956 at FIG. 9B) as determined via a test meter. It may be understood that the example graph at FIG. 9B relates to the data depicted at FIG. 9A.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A system, comprising:
a first glucose biosensor;
a second glucose biosensor; and
a mobile computing device, the mobile computing device including a processor, the processor storing instructions in non-transitory memory that, when executed, cause the processor to:
receive a notification that the second glucose biosensor has been inserted into a subject while the first glucose biosensor is already inserted into the subject;
initiate a cross calibration procedure within a determined amount of time subsequent to receiving the notification;
obtain a first current from the first glucose biosensor and a second current from the second glucose biosensor;
convert the first current to a first glucose value;
predict a background current associated with the second glucose biosensor based at least in part on the first current, the second current and the first glucose value;
subtract the background current from the second current to obtain a subtracted second current;
convert the subtracted second current to a second glucose value based on a conversion operation;
compare the first glucose value to the second glucose value to obtain an indication that the second glucose value is correlated within a predetermined threshold of the first glucose value; and
provide an alert that the first glucose biosensor can be removed in response to the indication that the second glucose value is correlated within the predetermined threshold of the first glucose value.

2. The system of claim 1, further comprising:
an insulin delivery unit in communication with the mobile computing device, the insulin delivery unit including at least an insulin pump and an infusion set, the infusion set fluidically coupled to the insulin pump via a tubing;
wherein the instructions, when executed by the processor, cause the processor to provide a set of instructions pertaining to delivery of insulin to the subject based on the second glucose value, and to send the set of instructions to the insulin delivery unit for delivering insulin to the subject via the infusion set by controlling operation of the insulin pump.

3. The system of claim 1, wherein the mobile computing device further comprises:
a display;
wherein the instructions, when executed by the processor, cause the processor to communicate a set of instructions pertaining to delivery of insulin to the subject via the display, and the set of instructions is based on the second glucose value.

4. The system of claim 1, wherein the instructions, when executed by the processor, cause the processor to:
provide a set of instructions pertaining to delivery of insulin to the subject based on the second glucose value, and responsive to the indication that the second glucose value is correlated within the predetermined threshold of the first glucose value.

5. The system of claim 1, wherein the alert is provided on a display screen of the mobile computing device.

6. The system of claim 1, wherein the instructions, when executed by the processor, cause the processor to:
predict the background current between one minute and 60 minutes following initiation of the cross calibration procedure; and
subtract the background current from the second current and convert the subtracted second current to the second glucose value based on the conversion operation for up to two days following initiation of the cross calibration procedure.

7. The system of claim 1, wherein the alert comprises at least one of an audible alert or a visual alert.

8. The system of claim 1, wherein the alert is sent to an application on a phone.

9. The system of claim 1, wherein the instructions, when executed by the processor, cause the processor to calibrate the first glucose biosensor prior to the initiation of the cross calibration procedure.

10. The system of claim 1, wherein the conversion operation is based at least in part on one or more of the first current or the first glucose value.

11. A computing device, comprising:
a memory to store instructions; and
a processor to execute the instructions to:
receive a notification that a second glucose biosensor has been inserted into a subject while a first glucose biosensor is already inserted into the subject;
initiate a cross calibration procedure in response to receiving the notification;
obtain a first current from the first glucose biosensor and a second current from the second glucose biosensor;
convert the first current to a first glucose value;
predict a background current associated with the second glucose biosensor based at least in part on the first current, the second current and the first glucose value;
subtract the background current from the second current to obtain a subtracted second current;
convert the subtracted second current to a second glucose value;
convert the subtracted second current to the second glucose value based on a conversion operation;
obtain an indication that the second glucose value is correlated within a predetermined threshold of the first glucose value; and
provide an alert in response to the indication that the second glucose value is correlated within the predetermined threshold of the first glucose value, wherein the alert indicates the first glucose biosensor can be removed from the subject.

12. The computing device of claim 11, wherein the conversion operation is based at least in part on one or more of the first current or the first glucose value.

13. The computing device of claim 11, wherein the alert comprises at least one of an audible alert or a visual alert.

14. The computing device of claim 11, wherein the alert is sent to an application on a phone.

15. The computing device of claim 11, wherein the instructions, when executed by the processor, cause the processor to:
send instructions pertaining to delivery of insulin to the subject to an insulin delivery unit, responsive to the indication that the second glucose value is correlated within the predetermined threshold of the first glucose value, the instructions sent to the insulin delivery unit are based on the second glucose value.

16. The computing device of claim 11, wherein the instructions, when executed by the processor, cause the processor to:
send instructions pertaining to delivery of insulin to the subject to a display screen for viewing by a user, responsive to the indication that the second glucose value is correlated within the predetermined threshold of the first glucose value, the instructions sent to the display screen are based on the second glucose value.

* * * * *